(12) United States Patent
Handler

(10) Patent No.: US 7,129,083 B1
(45) Date of Patent: *Oct. 31, 2006

(54) PIGGYBAC TRANSFORMATION SYSTEM

(75) Inventor: Alfred M. Handler, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 177 days.

This patent is subject to a terminal disclaimer.

(21) Appl. No.: 09/915,840

(22) Filed: Jul. 27, 2001

Related U.S. Application Data

(60) Provisional application No. 60/225,827, filed on Aug. 17, 2000.

(51) Int. Cl.
*C12N 15/63* (2006.01)
*C12N 15/11* (2006.01)
*C07H 21/04* (2006.01)

(52) U.S. Cl. ............... 435/320.1; 536/23.1; 536/24.1; 536/24.2

(58) Field of Classification Search ............... 435/69.1, 435/320.1, 455, 325, 91.4; 536/23.1, 24.1, 536/24
See application file for complete search history.

(56) References Cited

U.S. PATENT DOCUMENTS 6,218,185 B1 * 4/2001 Shirk et al. ................ 435/455

OTHER PUBLICATIONS

Handler, et al. Insect Molecular Biology. Nov. 1999, vol. 8, No. 4, pp. 449-457.*
O'Brochta et al., "Transposable Elements and Gene Transformation in Non-Drosophilid Insects", *Insect Biochemistry Molecular Biology*, vol. 26(8-9), pp. 739-753, 1996.
Lis et al., "New Heat Shock Puffs and β-Galactosidase Activity Resulting from Transformation of Drosophila with an hsp70—lacZ Hybrid Gene", *Cell*, vol. 35, pp. 403-410, 1983 (Part 1).
Lohe et al., "Germline Transformation of *Drosophila virilis* with the Transposable Element *mariner*", *Genetics*, vol. 143, pp. 365-374, 1996.
Loukeris et al., "Gene Transfer into the Medfly, *Ceratitis capitata* with a *Drosophila hydei* Transposable Element", *Science*, vol. 270, pp. 2002-2005, 1995.
Lozovskaya et al., "Germline Transformation of *Drosophila virilis* Mediated by the Transposable Element *hobo*", *Genetics*, vol. 142, pp. 173-177, 1996.
O'Brochta et al., "*Hermes*, a Functional Non-Drosophilid Insect Gene Vector From *Musca domestica*", *Genetics*, vol. 142, pp. 907-914, 1996.
Pirrotta et al., "Muliple upstream regulatory elements control the expression of the *Drosophila white* gene", *EMBO Journal*, vol. 4(13A), pp. 3501-3508, 1985.
Ashburner et al., "Prospects for the genetic transformation of arthropods", *Insect Molecular Biology*, vol. 7(3), pp. 201-213, 1998.
Bhadra et al., "Interactions Among Dosage-Dependent Trans-Acting Modifiers of Gene Expression and Position-Effect Variegation in Drosphila", *Genetics*, vol. 150, pp. 251-263, 1998.
Coates et al., "Mariner transposition and transformation of the yellow fever mosquito, *Aedes aegypti*", *Genetics*, vol. 95, pp. 3748-3751, 1998.
Chalfie et al., "Green Fluorescent Protein as a Marker for Gene Expression", *Science*, vol. 63, pp. 802-805, 1994.
Cormack et al., "ACS-optimized mutants of the green fluorescent protein (GFP)", *Science*, vol. 173, pp. 33-38, 1996.
Davis et al., "A Nuclear GFP that Marks Nuclei in Living *Drosophila* Embryos; Maternal Supply Overcomes a Delay in the Appearance of Zygotic Fluorescence", *Developmental Biology*, vol. 170, pp. 726-729, 1995.
Elick et al., "PCR analysis of insertion site specificity, transcription, and structural uniformity of the Lepidopteran transposable element IFP2 in the TN-368 cell genome", *Genetica*, vol. 97, pp. 127-139, 1996.
Franz et al., "Mobile Minos elements from *Drosophila hydei* encode a two-exon transposase with similarity to the paired DNA-binding domain", *Proc. Natl. Acad. Science*, vol. 91, pp. 4746-4750, 1994.
Gomez et al., "A *Drosophila melanogaster* hobo-white+ vector mediates low frequency gene transfer in *D. virilis* with full interspecific white$^+$ complementation", *Insect Molecular Biology*, vol. 6(2), pp. 165-171, 1997.
Hazelrigg et al., "Transformation of white Locus DNA in *Drosophila*: Dosage Compensation, zeste Interaction, and Position Effects", *Cell*, vol. 36, pp. 469-481, 1984.
Jacobson et al., "Molecular structure of a somatically unstable transposable element in *Drosophila*", *Proc. Natl. Acad. Science*, vol. 83, pp. 8684-8688, 1986.
Jasinskiene et al., "Stable transformation of the yellow fever mosquito, *Aedes aegypti*, with the *Hermes* element from the housefly", *Genetics*, pp. 3743-3747, 1998.
Lanford et al., "Induction of Nuclear Transport with a Synthetic Peptide Homologous to the SV40 Antigen Transport Signal", *Cell*, vol. 46, pp. 575-582, 1986.

(Continued)

Primary Examiner—David Guzo
Assistant Examiner—Ramin (Ray) Akhavan
(74) Attorney, Agent, or Firm—John D. Fado; Gail E. Poulos

(57) ABSTRACT

The present invention is directed to a transformation systems and vectors for making transgenic organisms that includes a vector containing a modified piggyBac transposon into which is inserted at least one fluorescent protein gene linked to a polyubiquitin promoter sequence. A helper transposase vector that includes an hsp70 promoter sequence upstream of the putative piggyBac promoter that increases the transformation frequency of this system can also be included.

2 Claims, 26 Drawing Sheets
(9 of 26 Drawing Sheet(s) Filed in Color)

OTHER PUBLICATIONS

Lee et al., "Structure and Expression of Ubiquitin Genes of *Drosophila melanogaster*", *Molecular and Cellular Biology*, vol. 8(11), pp. 4727-4735, 1988.

Lidholm et al., "The Transposable Element mariner Mediates Germline Transformation in *Drosophila melanogaster*", *Genetics*, vol. 134, pp. 859-868, 1993.

Franz et al., "Minos, a new transposable element from *Drosophila hydei*, is a member of the Tc1-like family of transposons", *Nucleic Acids Research*, vol. 19(23), p. 646, 1991.

Prasher et al., "Primary structure of the *Aequorea vistoria* green-fluorescent protein", *Gene*, vol. 111, pp. 229-233, 1992.

Rubin et al., "Genetic Transformation of *Drosophila* with Transposable Element Vectors", *Science*, vol. 218, pp. 348-353, 1982.

Smith et al., "hobo Enhancer Trapping Mutagenesis in *Drosophila* Reveals an Insertion Specificity Different from P Elements", *Genetics*, vol. 135, pp. 1063-1076, 1993.

Wang et al., "Implications for bcd mRNA localization from spatial distribution of exu protein in *Drosophila* oogenesis", *Nature*, vol. 369, pp. 400-403, 1994.

Warren et al., "The Hermes transposable element from the house fly, *Musca domestrica*, is a short inverted repeat-type element of the *hobo*, *Ac*, and *Tam3* (*hAT*) element family", pp. 87-97, 1994.

Ahmed et al., "Use of ordered deletions in genome sequencing", *Gene*, vol. 197, pp. 367-373, 1997.

Cary et al., "Transposon Mutagenesis of Baculoviruses: Analysis of *Trichoplusia ni* Transposon IFP2 Insertions within the FP-Locus of Nuclear Polyhedrosis Viruses", *Virology*, vol. 172, pp. 156-169, 1989.

Yang et al., "Optimized codon usage and chromophore mutations provide enhanced sensitivity with the green fluorescent protein", *Nucleic Acids Research*, vol. 24(22), pp. 4592-4593, 1996.

Handler et al., "The lepidopteran transposon vector, *piggyBac*, mediates germ-line transformation in the Mediterranean fruit fly", *Proc. Natl. Acad. Science USA*, vol. 95, pp. 7520-7525, 1998.

Handler, A.M., et al., "The PiggyBac Transposon Mediates Germ-line Transformation in the Oriental Fruit Fly and Closely Related Elements Exist in its Genome", *Insect Molecular Biology*, vol. 9, (6), pp. 605-612, 2000.

Handler, A., et al., "Transformation of the Caribbean Fruit Fly, *Anastrepha suspensa*, with a PiggyBac Vector Marked with Polyubiquitin-regulated GFP", *Insect Biochemistry and Mol. Biology*, vol. 31, pp. 199-205, 2001.

Handler, A., et al., "Polyubiquitin-Regulated DsRed Marker for Transgenic Insects", *Biotechniques*, vol. 31, (3), pp. 2-6, 2001.

Handler, A., "A Current Perspective on Insect Gene Transformation", *Insect Biochemistry and Molecular Biology*, vol. 31, pp. 111-128, 2001.

* cited by examiner

| | | |
|---|---|---|
| p3E1.2 | aagcgcaaatcttttTTAA-*piggyBac*-TTAAataatagtttctaat | |
| F1-2 | aaaaagactgactatTTAA-*piggyBac*-TTAAtaagcacactgagtc | |
| M17-4 | aaaatgtcgtctaggTTAA-*piggyBac*-TTAAagccgtatatcagat | |
| M31-6 | aaatgaacgacttttTTAA-*piggyBac*-TTAAtggttttttagttgt | |

FIG. 4b

|  | 10 | 20 | 30 | 40 | 50 |  |
|---|---|---|---|---|---|---|
|  | 1234567890 | 1234567890 | 1234567890 | 1234567890 | 1234567890 |  |
|  | GACGAAAGGG | CCTCGTGATA | CGCCTATTTT | TATAGGTTAA | TGTCATGATA | 50 |
|  | ATAATGGTTT | CTTAGACGTC | AGGTGGCACT | TTTCGGGGAA | ATGTGCGCGG | 100 |
|  | AACCCCTATT | TGTTTATTTT | TCTAAATACA | TTCAAATATG | TATCCGCTCA | 150 |
|  | TGAGACAATA | ACCCTGATAA | ATGCTTCAAT | AATATTGAAA | AGGAAGAGT | 200 |
|  | ATGAGTATTC | AACATTTCCG | TGTCGCCCTT | ATTCCCTTTT | TTGCGGCATT | 250 |
|  | TTGCCTTCCT | GTTTTGCTC | ACCCAGAAAC | GCTGGTGAAA | GTAAAAGATG | 300 |
|  | CTGAAGATCA | GTTGGGTGCA | CGAGTGGGTT | ACATCGAACT | GGATCTCAAC | 350 |
|  | AGCGGTAAGA | TCCTTGAGAG | TTTTCGCCCC | GAAGAACGTT | TTCCAATGAT | 400 |
|  | GAGCACTTTT | AAAGTTCTGC | TATGTGGCGC | GGTATTATCC | CGTATTGACG | 450 |
|  | CCGGGCAAGA | GCAACTCGGT | CGCCGCATAC | ACTATTCTCA | GAATGACTTG | 500 |
|  | GTTGAGTACT | CACCAGTCAC | AGAAAAGCAT | CTTACGGATG | GCATGACAGT | 550 |
|  | AAGAGAATTA | TGCAGTGCTG | CCATAACCAT | GAGTGATAAC | ACTGCGGCCA | 600 |
|  | ACTTACTTCT | GACAACGATC | GGAGGACCGA | AGGAGCTAAC | CGCTTTTTTG | 650 |
|  | CACAACATGG | GGGATCATGT | AACTCGCCTT | GATCGTTGGG | AACCGGAGCT | 700 |
|  | GAATGAAGCC | ATACCAAACG | ACGAGCGTGA | CACCACGATG | CCTGTAGCAA | 750 |
|  | TGGCAACAAC | GTTGCGCAAA | CTATTAACTG | GCGAACTACT | TACTCTAGCT | 800 |
|  | TCCCGGCAAC | AATTAATAGA | CTGGATGGAG | GCGGATAAAG | TTGCAGGACC | 850 |
|  | ACTTCTGCGC | TCGGCCCTTC | CGGCTGGCTG | GTTTATTGCT | GATAAATCTG | 900 |
|  | GAGCCGGTGA | GCGTGGGTCT | CGCGGTATCA | TTGCAGCACT | GGGGCCAGAT | 950 |
|  | GGTAAGCCCT | CCCGTATCGT | AGTTATCTAC | ACGACGGGGA | GTCAGGCAAC | 1000 |
|  | TATGGATGAA | CGAAATAGAC | AGATCGCTGA | GATAGGTGCC | TCACTGATTA | 1050 |
|  | AGCATTGGTA | ACTGTCAGAC | CAAGTTTACT | CATATATACT | TTAGATTGAT | 1100 |
|  | TTAAAACTTC | ATTTTTAATT | TAAAAGGATC | TAGGTGAAGA | TCCTTTTTGA | 1150 |
|  | TAATCTCATG | ACCAAAATCC | CTTAACGTGA | GTTTTCGTTC | CACTGAGCGT | 1200 |
|  | CAGACCCCGT | AGAAAAGATC | AAAGGATCTT | CTTGAGATCC | TTTTTTTCTG | 1250 |
|  | CGCGTAATCT | GCTGCTTGCA | ACAAAAAAAA | CCACCGCTAC | CAGCGGTGGT | 1300 |
|  | TTGTTTGCCG | GATCAAGAGC | TACCAACTCT | TTTTCCGAAG | GTAACTGGCT | 1350 |
|  | TCAGCAGAGC | GCAGATACCA | AATACTGTCC | TTCTAGTGTA | GCCGTAGTTA | 1400 |
|  | GGCCACCACT | TCAAGAACTC | TGTAGCACCG | CCTACATACC | TCGCTCTGCT | 1450 |
|  | AATCCTGTTA | CCAGTGGCTG | CTGCCAGTGG | CGATAAGTCG | TGTCTTACCG | 1500 |
|  | GGTTGGACTC | AAGACGATAG | TTACCGGATA | AGGCGCAGCG | GTCGGGCTGA | 1550 |
|  | ACGGGGGGTT | CGTGCACACA | GCCCAGCTTG | GAGCGAACGA | CCTACACCGA | 1600 |
|  | ACTGAGATAC | CTACAGCGTG | AGCATTGAGA | AAGCGCCACG | CTTCCCGAAG | 1650 |
|  | GGAGAAAGGC | GGACAGGTAT | CCGGTAAGCG | GCAGGGTCGG | AACAGGAGAG | 1700 |
|  | CGCACGAGGG | AGCTTCCAGG | GGGAAACGCC | TGGTATCTTT | ATAGTCCTGT | 1750 |
|  | CGGGTTTCGC | CACCTCTGAC | TTGAGCGTCG | ATTTTTGTGA | TGCTCGTCAG | 1800 |

FIG. 6a

|          10         20         30         40         50      |      |
| 1234567890 1234567890 1234567890 1234567890 1234567890 |      |
| GGGGCGGAG CCTATGGAAA AACGCCAGCA ACGCGGCCTT TTTACGGTTC | 1850 |
| CTGGCCTTTT GCTGGCCTTT TGCTCACATG TTCTTTCCTG CGTTATCCCC | 1900 |
| TGATTCTGTG GATAACCGTA TTACCGCCTT TGAGTGAGCT GATACCGCTC | 1950 |
| GCCGCAGCCG AACGACCGAG CGCAGCGAGT CAGTGAGCGA GGAAGCGGAA | 2000 |
| GAGCGCCCAA TACGCAAACC GCCTCTCCCC GCGCGTTGGC CGATTCATTA | 2050 |
| ATGCAGCTGG CACGACAGGT TTCCCGACTG GAAAGCGGGC AGTGAGCGCA | 2100 |
| ACGCAATTAA TGTGAGTTAG CTCACTCATT AGGCACCCCA GGCTTTACAC | 2150 |
| TTTATGCTTC CGGCTCGTAT GTTGTGTGGA ATTGTGAGCG GATAACAATT | 2200 |
| TCACACAGGA AACAGCTATG ACCATGATTA CGAATTCGAG CTCGGTACCC | 2250 |
| GGGGATCCTC TAGAGTCGAC CTGCAGGCAT GCAAGCTTGC ATGCCTGCAG | 2300 |
| GTCGACGCTC GCGCGACTTG GTTTGCCATT CTTTAGCGCG CGTCGCGTCA | 2350 |
| CACAGCTTGG CCACAATGTG GTTTTTGTCA AACGAAGATT CTATGACGTG | 2400 |
| TTTAAAGTTT AGGTCGAGTA AAGCGCAAAT CTTTTTTAAC CCTAGAAAGA | 2450 |
| TAGTCTGCGT AAAATTGACG CATGCATTCT TGAAATATTG CTCTCTCTTT | 2500 |
| CTAAATAGCG CGAATCCGTC GCTGTGCATT TAGGACATCT CAGTCGCCGC | 2550 |
| TTGGAGCTCC CGTGAGGCGT GCTTGTCAAT GCGGTAAGTG TCACTGATTT | 2600 |
| TGAACTATAA CGACCGCGTG AGTCAAAATG ACGCATGATT ATCTTTTACG | 2650 |
| TGACTTTTAA GATTTAACTC ATACGATAAT TATATTGTTA TTTCATGTTC | 2700 |
| TACTTACGTG ATAACTTATT ATATATATAT TTTCTTGTTA TAGATATCGT | 2750 |
| GACTAATATA TAATAAAATG GGTAGTTCTT TAGACGATGA GCATATCCTC | 2800 |
| TCTGCTCTTC TGCAAAGCGA TGACGAGCTT GTTGGTGAGG ATTCTGACAG | 2850 |
| TGAAATATCA GATCACGTAA GTGAAGATGA CGTCCAGAGC GATACAGAAG | 2900 |
| AAGCGTTTAT AGATGAGGTA CATGAAGTGC AGCCAACGTC AAGCGGTAGT | 2950 |
| GAAATATTAG ACGAACAAAA TGTTATTGAA CAACCAGGTT CTTCATTGGC | 3000 |
| TTCTAACAGA ATCTTGACCT TGCCACAGAG GACTATTAGA GGTAAGAATA | 3050 |
| AACATTGTTG GTCAACTTCA AAGTCCACGA GGCGTAGCCG AGTCTCTGCA | 3100 |
| CTGAACATTG TCAGATCTCG AGCTCAAGCT TGAATTCTG CAGTCGACGG | 3150 |
| TACCCGATCT TGTCGCCGGA ACGCAGCGAC AGAGATTCCA ATGTGTCCGT | 3200 |
| ATCTTTCAGG CTTTTGCCCT TCAGTTCCAG ACGAAGCGAC TGGCGATTCG | 3250 |
| CGTGTGGGGT CTGCTTCAGG GTCTTGTGAA TTAGGGCGCG CAGATCGCCG | 3300 |
| ATGGGCGTGG CGCCGGAGGG CACCTTCACC TTGCCGTACG GCTTGCTGTT | 3350 |
| CTTGCCGTTC AAAATCTCCA GCTCCATTTT GCTTTCGGTG CGCTTGCAAT | 3400 |
| CAGTACTGTC CAAAATCGAA AATCGCCGAA CCGTAGTGTG ACCGTGCGGG | 3450 |
| GCTCTGCCGAA AATAAACTTT TTAGGTATA TGGCCACACA CGGGAAAGC | 3500 |
| ACAGTGGATT ATATGTTTTA ATATTATAAT ATGCAGGTTT TCATTACTTA | 3550 |
| TCCAGATGTA AGCCCACTTA AAGCGATTTA ACAATTATTT GCCGAAAGAG | 3600 |

Fig. 6b

```
          10         20         30         40         50
  1234567890 1234567890 1234567890 1234567890 1234567890
  TAAAAACAAA TTTCACTTAA AAATGGATTA AGAAAAGCTT GTGTAAGATT  3650
  ATGCGCAGCG TTGCCAGATA GCTCCATTTA AAACACTTCA AAAACAATAA  3700
  GTTTTGAAAA TATATACATA AATAGCAGTC GTTGCCGCAA CGCTCAACAC  3750
  ATCACACTTT TAAAACACCC TTTACCTACA CAGAATTACT TTTTAAATTT  3800
  CCAGTCAAGC TGCGAGTTTC AAAATTATAG CCGGTAGAGA AGACAGTGCT  3850
  ATTTCAAAAG CAAACTAAAT AAACACCAAT CCTAACAAGC CTTGGACTTT  3900
  TGTAAGTTTA GATCAAAGGT GGCATTGCAT TCAATGTCAT GGTAAGAAGT  3950
  AGGTCGTCTA GGTAGAAATC CTCATTCAGC CGGTCAAGTC AGTACGAGAA  4000
  AGGTCTCAAT TTGAAATTGT CTTAAAAATA TTTTATTGTT TTGTACTGTG  4050
  GTGAGTTTAA ACGAAAAACA CAAAAAAAAA GTGATACACA GAAATCATAA  4100
  AAAATTTTAA TACAAGGTAT TCGTACGTAT CAAAAACATT TCGGCACAAT  4150
  TTTTTTTCTC TGTACTAAAG TGTTACGAAC ACTACGGTAT TTTTTAGTGA  4200
  TTTTCAACGG ACACCGAAGG TATATAAACA CCGTTCGCGA ACGGTCGCCT  4250
  TCAAAACCAA TTGACATTTG CAGCAGCAAG TACAAGCAGA AGTAAAGCG   4300
  CAATCAGCGA AAAATTTATA CTTAATTGTT GGTGATTAAA GTACAATTAA  4350
  AAGAACATTC TCGAAAGTCA CAAGAAACGT AAGTTTTTAA CTCGCTGTTA  4400
  CCAATTAGTA ATAAGAGCAA CAAGACGTTG AGTAATTTCA AGAAAAACTG  4450
  CATTTCAAGG TCTTTGTTCG GCCATTTTTT TTTTATTCAA CGCTCTACGT  4500
  AATTACAAAA TAAGAAATTG GCAGCCACGC ATCTTGTTTT CCCAATCAAT  4550
  TGGCATCAAA ACGCAAACAA ATCTATAAAT AAAACTTGCG TGTTGATTTT  4600
  CGCCAAGATT TATTGGCAAA TTGTGAAATT CGCAGTGACG CATTTGAAAA  4650
  TTCGAGAAAT CACGAACGCA CTCGAGCATT TGTGTGCATG TTATTAGTTA  4700
  GTTAGTTCTT TGCTTAATTG AAGTATTTTA CCAACGAAAT CCACTTATTT  4750
  TTAGCTGAAA TAGAGTAGGT TGCTTGAAAC GAAAGCCACG TCTGGAAAAT  4800
  TTCTTATTGC TTAGTAGTTG TGACGTCACC ATATACACAC AAAATAATGT  4850
  GTATGCATGC GTTTCAGCTG TGTATATATA CATGCACACA CTCGCATTAT  4900
  GAAAACGATG ACGAGCAACG GAACAGGTTT CTCAACTACC TTTGTTCCTG  4950
  TTTCTTCGCT TTCCTTTGTT CCAATATTCG TAGAGGGTTA ATAGGGGTTT  5000
  CTCAACAAAG TTGGCGTCGA TAAATAAGTT TCCCATTTTT ATTCCCCAGC  5050
  CAGGAAGTTA GTTTCAATAG TTTTGTAATT TCAACGAAAC TCATTTGATT  5100
  TGTACTAAT TTTCCACATC TCTATTTTGA CCCGCAGAAT AATCCAAAAT   5150
  GCAGATCGGG GATCCACCC CACCCAAGAA GAAGCGCAAG GTGGAGGACG   5200
  ATCCCGTCGT TTTACAACGT CGTGACTGGG AAAACCCTGG CGTTACCCAA  5250
  CTTAATCGCC TTGCAGCACA TCCCCCTTTC GCCAGCTGGC GTAATAGCGA  5300
  AGAGGCCCGC ACCGATCGCC CTTCCCAACA GTTGCGGTCG ACTCTAGAGG  5350
  ATCCCCGGGA TCCACCGGTC GCCACCATGG TGAGCAAGGG CGAGGAGCTG  5400
```

Fig. 6c

|     | 10         | 20         | 30         | 40         | 50         |      |
|-----|------------|------------|------------|------------|------------|------|
|     | 1234567890 | 1234567890 | 1234567890 | 1234567890 | 1234567890 |      |
| TTCACCGGGG | TGGTGCCCAT | CCTGGTCGAG | CTGGACGGCG | ACGTAAACGG | 5450 |
| CCACAAGTTC | AGCGTGTCCG | GCGAGGGCGA | GGGCGATGCC | ACCTACGGCA | 5500 |
| AGCTGACCCT | GAAGTTCATC | TGCACCACCG | GCAAGCTGCC | CGTGCCCTGG | 5550 |
| CCCACCCTCG | TGACCACCCT | GACCTACGGC | GTGCAGTGCT | TCAGCCGCTA | 5600 |
| CCCCGACCAC | ATGAAGCAGC | ACGACTTCTT | CAAGTCCGCC | ATGCCCGAAG | 5650 |
| GCTACGTCCA | GGAGCGCACC | ATCTTCTTCA | AGGACGACGG | CAACTACAAG | 5700 |
| ACCCGCGCCG | AGGTGAAGTT | CGAGGGCGAC | ACCCTGGTGA | ACCGCATCGA | 5750 |
| GCTGAAGGGC | ATCGACTTCA | AGGAGGACGG | CAACATCCTG | GGCACAAGC  | 5800 |
| TGGAGTACAA | CTACAACAGC | CACAACGTCT | ATATCATGGC | CGACAAGCAG | 5850 |
| AAGAACGGCA | TCAAGGTGAA | CTTCAAGATC | CGCCACAACA | TCGAGGACGG | 5900 |
| CAGCGTGCAG | CTCGCCGACC | ACTACCAGCA | GAACACCCCC | ATCGGCGACG | 5950 |
| GCCCCGTGCT | GCTGCCCGAC | AACCACTACC | TGAGCACCCA | GTCCGCCCTG | 6000 |
| AGCAAGACC  | CCAACGAGAA | GCGCGATCAC | ATGGTCCTGC | TGGAGTTCGT | 6050 |
| GACCGCCGCC | GGGATCACTC | TCGGCATGGA | CGAGCTGTAC | AAGTAAAGCG | 6100 |
| GCCGCGACTC | TAGATCATAA | TCAGCCATAC | CACATTTGTA | GAGGTTTTAC | 6150 |
| TTGCTTTAAA | AAACCTCCCA | CACCTCCCC  | TGAACCTGAA | ACATAAAATG | 6200 |
| AATGCAATTG | TTGTTGTTAA | CTTGTTTATT | GCAGCTTATA | ATGGTTACAA | 6250 |
| ATAAAGCAAT | AGCATCACAA | ATTTCACAAA | TAAAGCATTT | TTTCACTGC  | 6300 |
| ATTCTAGTTG | TGGTTTGTCC | AAACTCATCA | ATGTATCTTA | AGGCGTAAAT | 6350 |
| TGTAAGCGTT | AATATTTTGT | TAAAATTCGC | GTTAAATTTT | TGTTAAATCA | 6400 |
| GCTCATTTTT | TAACCAATAG | GCCGAAATCG | GCAAAATCCC | TTATAAATCA | 6450 |
| AAAGAATAGA | CCGAGATAGG | GTTGAGTGTT | GTTCCAGTTT | GGAACAAGAG | 6500 |
| TCCACTATTA | AAGAACGTGG | ACTCCAACGT | CAAAGGGCGA | AAAACCGTCT | 6550 |
| ATCAGGGCGA | TGGCCCACTA | CGTGAACCAT | CACCCTAATC | AAGTTTTTTG | 6600 |
| GGGTCGAGGT | GCCGTAAAGC | ACTAAATCGG | AACCCTAAAG | GGAGCCCCG  | 6650 |
| ATTTAGAGCT | TGACGGGGAA | AGCCGGCGAA | CGTGGCGAGA | AAGGAAGGGA | 6700 |
| AGAAAGCGAA | AGGAGCGGGC | GCTAGGGCGC | TGGCAAGTGT | AGCGGTCACG | 6750 |
| CTGCGCGTAA | CCACCACACC | CGCCGCGCTT | AATGCGCCGC | TACAGGGCGC | 6800 |
| GTCAGGTGGC | ACTTTTCGGG | GAAATGTGCG | CGGAACCCCT | ATTTGTTTAT | 6850 |
| TTTTCTAAAT | ACATTCAAAT | ATGTATCCGC | TCATGAGACA | ATAACCCTGA | 6900 |
| TAAATGCTTC | AATAATATTG | AAAAAGGAAG | AGTCCTGAGG | CGGAAAGAAC | 6950 |
| CAGCTGTGGA | ATGTGTGTCA | GTTAGGGTGT | GGAAAGTCCC | CAGGCTCCCC | 7000 |
| AGCAGGCAGA | AGTATGCAAA | GCATGCATCT | CAATTAGTCA | GCAACCAGGT | 7050 |
| GTGGAAAGTC | CCCAGGCTCC | CCAGCAGGCA | GAAGTATGCA | AAGCATGCAT | 7100 |
| CTCAATTAGT | CAGCAACCAT | AGTCCCGCCC | CTAACTCCGC | CCATCCCGCC | 7150 |
| CCTAACTCCG | CCCAGTTCCG | CCCATTCTCC | GCCCCATGGC | TGACTAATTT | 7200 |

Fig. 6d

|  | 10 | 20 | 30 | 40 | 50 |  |
|---|---|---|---|---|---|---|
|  | 1234567890 | 1234567890 | 1234567890 | 1234567890 | 1234567890 |  |
|  | TTTTTATTTA | TGCAGAGGCC | GAGGCCGCCT | CGGCCTCTGA | GCTATTCCAG | 7250 |
|  | AAGTAGTGAG | GAGGCTTTTT | TGGAGGAACC | ATTGTGGGAA | CCGTGCGATC | 7300 |
|  | AAACAAACGC | GAGATACCGG | AAGTACTGAA | AAACAGTCGC | TCCAGGCCAG | 7350 |
|  | TGGAACATC | GATGTTTGT | TTTGACGGAC | CCCTTACTCT | CGTCTCATAT | 7400 |
|  | AAACCGAAGC | CAGCTAAGAT | GGTATACTTA | TTATCATCTT | GTGATGAGGA | 7450 |
|  | TGCTTCTATC | AACGAAAGTA | CCGGTAAACC | GCAAATGGTT | ATGTATTATA | 7500 |
|  | ATCAAACTAA | AGGCGGAGTG | GACACGCTAG | ACCAAATGTG | TTCTGTGATG | 7550 |
|  | ACCTGCAGTA | GGAAGACGAA | TAGGTGGCCT | ATGGCATTAT | TGTACGGAAT | 7600 |
|  | GATAAACATT | GCCTGCATAA | ATTCTTTTAT | TATATACAGC | CATAATGTCA | 7650 |
|  | GTAGCAAGGG | AGAAAAGGTC | CAAAGTCGCA | AAAAATTTAT | GAGAAACCTT | 7700 |
|  | TACATGAGCC | TGACGTCATC | GTTTATGCGT | AAGCGTTTAG | AAGCTCCTAC | 7750 |
|  | TTTGAAGAGA | TATTTGCGCG | ATAATATCTC | TAATATTTTG | CCAAATGAAG | 7800 |
|  | TGCCTGGTAC | ATCAGATGAC | AGTACTGAAG | AGCCAGTAAT | GAAAAAACGT | 7850 |
|  | ACTTACTGTA | CTTACTGCCC | CTCTAAAATA | AGGCGAAAGG | CAAATGCATC | 7900 |
|  | GTGCAAAAAA | TGCAAAAAG | TTATTTGTCG | AGAGCATAAT | ATTGATATGT | 7950 |
|  | GCCAAAGTTG | TTTCTGACTG | ACTAATAAGT | ATAATTTGTT | TCTATTATGT | 8000 |
|  | ATAAGTTAAG | CTAATTACTT | ATTTTATAAT | ACAACATGAC | TGTTTTTAAA | 8050 |
|  | GTACAAAATA | AGTTTATTTT | TGTAAAGAG | AGAATGTTTA | AAGTTTTGT | 8100 |
|  | TACTTTATAG | AAGAAATTTT | GAGTTTTTGT | TTTTTTTTAA | TAAATAAATA | 8150 |
|  | AACATAAATA | AATTGTTTGT | TGAATTTATT | ATTAGTATGT | AAGTGTAAAT | 8200 |
|  | ATAATAAAAC | TTAATATCTA | TTCAAATTAA | TAAATAAACC | TCGATATACA | 8250 |
|  | GACCGATAAA | ACACATGCGT | CAATTTTACG | CATGATTATC | TTTAACGTAC | 8300 |
|  | GTCACAATAT | GATTATCTTT | CTAGGGTTAA | ATAATAGTTT | CTAATTTTTT | 8350 |
|  | TATTATTCAG | CCTGCTGTCG | TGAATACCGT | ATATCTCAAC | GCTGTCTGTG | 8400 |
|  | AGATTGTCGT | ATTCTAGCCT | TTTTAGTTTT | TGCCTCATCG | ACTTGATATT | 8450 |
|  | GTCCGACACA | TTTTCGTCGA | TTTGCGTTTT | GATCAAAGAC | TTGAGCAGAG | 8500 |
|  | ACACGTTAAT | CAACTGTTCA | AATTGATCCA | TATTAACGAT | ATCAACCCGA | 8550 |
|  | TGCGTATATG | GTGCGTAAAA | TATATTTTTT | AACCCTCTTA | TACTTTGCAC | 8600 |
|  | TCTGCGTTAA | TACGCGTTCG | TGTACAGACG | TAATCATGTT | TTCTTTTTTG | 8650 |
|  | GATAAAACTC | CTACTGAGTT | TGACCTCATA | TTAGACCCTC | ACAAGTTGCA | 8700 |
|  | AAACGTGGCA | TTTTTTACCA | ATGAAGAATT | TAAAGTTATT | TTAAAAAATT | 8750 |
|  | TCATCACAGA | TTTAAGAAG | AACCAAAAAT | TAAATTATTT | CAACAGTTTA | 8800 |
|  | ATCGACCAGT | TAATCAACGT | GTACACAGAC | GCGTCGGCAA | AAAACACGCA | 8850 |
|  | GCCCGACGTG | TTGGCTAAAA | TTATTAAATC | AACTTGTGTT | ATAGTCACGG | 8900 |
|  | ATTTGCCGTC | CAACGTGTTC | CTCAAAAAGT | TGAAGACCAA | CAAGTTTACG | 8950 |
|  | GACACTATTA | ATTATTTGAT | TTTGCCCCAC | TTCATTTTGT | GGGATCACAA | 9000 |

FIG. 6e

```
          10         20         30         40         50
  1234567890 1234567890 1234567890 1234567890 1234567890
  TTTTGTTATA TTTTAAACAA AGCTTGGCAC TGGCCGTCGT TTTACAACGT   9050
  CGTGACTGGG AAAACCCTGG CGTTACCCAA CTTAATCGCC TTGCAGCACA   9100
  TCCCCCTTTC GCCAGCTGGC GTAATAGCGA AGAGGCCCGC ACCGATCGCC   9150
  CTTCCCAACA GTTGCGCAGC CTGAATGGCG AATGGCGCCT GATGCGGTAT   9200
  TTTCTCCTTA CGCATCTGTG CGGTATTTCA CACCGCATAT GGTGCACTCT   9250
  CAGTACAATC TGCTCTGATG CCGCATAGTT AAGCCAGCCC CGACACCCGC   9300
  CAACACCCGC TGACGCGCCC TGACGGGCTT GTCTGCTCCC GGCATCCGCT   9350
  TACAGACAAG CTGTGACCGT CTCCGGGAGC TGCATGTGTC AGAGGTTTTC   9400
  ACCGTCATCA CCGAAACGCG CGA                               9423
```

PIGGYBAC TRANSFORMATION SYSTEM

This application claims benefit to copending provisional application Ser. No. 60/225,827, filed Aug. 17, 2000; which is herein incorporated by reference.

BACKGROUND OF INVENTION

1. Field of the Invention

This invention relates to a transformation system that includes a gene transfer vector containing a modified piggyBac transposon (pB) and having the insertion of a marker construct containing at least one fluorescent protein gene linked to a polyubiquitin promoter gene. The invention further relates to a helper vector containing a heat shock protein gene and to methods for using this system to transform eukaryotic cells as well as transgenic organisms produced using the system, especially insect cells and insects, respectively.

2. Description of the Related Art

The piggyBac transposable element from the cabbage looper moth, *Trichoplusia ni* (Cary et al., Virology, Volume 161, 8–17, 1989) has been shown to be an effective gene-transfer vector in the Mediterranean fruit fly, *Ceratitis capitata* (Handler et al., Proc. Natl. Acad. Sci. USA, Volume 95, 7520–7525, 1998). Use of an unmodified transposase helper under piggyBac promoter regulation indicates that piggyBac retains autonomous function in the medfly, since transcriptional regulation was maintained, as well as enzymatic activity. This observation was unique since all other successful insect germline transformations had been limited to dipteran species using vectors isolated from the same or another dipteran. The initial transformation of medfly (Loukeris et al., Science, Volume 270, 2002–2005, 1995) used the *Minos* vector from *Drosophila hydei* (Franz & Savakis, Nucl. Acids Res., Volume 19, 6646, 1991), and *Aedes aegypti* has been transformed from Hermes (Jasinskiene et al., Proc. Natl. Acad. Sci. USA, Volume 95, 3743–3747, 1998) from *Musca domestica* (Warren et al., Genet. Res. Camb., Volume 64, 87–97, 1994) and mariner (Coates et al., Proc. Natl. Acad. Sci. USA, Volume 95, 3748–3751, 1998) from *Drosophila mauritiana* (Jacobson et al., Proc. Natl. Acad. Sci. USA, Volume 83, 8684–8688, 1986). *Drosophila melanogaster* has been transformed as well by Hermes (O'Brochta et al., Insect Biochem. Molec. Biol., Volume 26, 739–753, 1996) mariner (Lidholm et al., Genetics, Volume 134, 859–868, 1993), Minos (Franz et al., Proc. Natl. Acad. Sci. USA, Volume 91, 4746–4750, 1994) and by the P and hobo transposons originally discovered in its own genome (Rubin and Spradling, 1989; Blackman et al., EMBO J., Volume 8, 211–217, 1989). *Drosophila virilis* also has been transformed by hobo (Lozovskaya et al., Genetics, Volume 143, 365–374, 1995; Gomez & Handler, Insect Mol. Biol., Volume 6, 1–8, 1997) and mariner (Lohe et al., Genetics, Volume 143, 365–374, 1996). While the restriction to dipteran vectors is due in part to the limited number of transposon systems available from non-dipteran species, phylogenetic limitations on transposon function is not unexpected considering the deleterious effects functional transposons may have on a host genome. This is, indeed, reflected by the high level of regulation placed on transposon movement among species, among strains within a host species, and even among cell types within an organism (Berg & Howe, *Mobile DNA*, American Society for Microbiology, Washington, D.C. 1989).

The ability of piggyBac to function in several dipteran species will be supportive of its use in a wider range of insects, if not other organisms. Most other vector systems function optimally, or have been only tested with their helper transposase under hsp70 promoter regulation. The transposition efficiency of most vectors has been also found to be influenced by the amount of internal DNA inserted, the position of this DNA within the vector, and the amount of subterminal DNA remaining in the vectors.

The widespread use of piggyBac will be limited by the availability of easily detectable and unambiguous transformant markers. Most *Drosophila* transformations, as well as the few nondrosophilid transformations reported have depended on transformant selection by rescue of a mutant visible phenotype, usually eye pigmentation (Ashburner et al., Insect Mol. Biol., Volume 7, 201–213, 1998). Unfortunately, most insect species have neither visible mutant strains, nor the cloned DNA for the wild type allele of the mutation, and these species require use of new dominant-acting marker genes that confer, preferably, a visible phenotype.

The present invention, discussed below, provides a system that includes vectors for transforming eukaryotic cells, derived from piggyBac transposons that are different from related art vectors. Furthermore, the present invention increases the transformation frequency by about eight-fold compared to other piggyBac transformation systems.

SUMMARY OF THE INVENTION

It is therefore an object of the present invention to provide a transformation system which contains a vector that includes DNA derived from a piggyBac transposon element that allows for the almost precise excision of at least a second DNA sequence that is heterologous and included in the construct and insertion of at least said second heterologous DNA sequence into eukaryotic cells after introduction of the transformation construct containing said first and at least a second DNA into said cell that is then used to form a transgenic organism wherein said transgenic organism is detectable under ultraviolet light.

Another object of the present invention is to provide a transformation system that includes a vector containing a modified piggyBac sequence, at least one sequence for marker expression linked to a polyubiquitin promoter and a helper vector including a heat shock protein gene wherein said system causes an increase in transformation frequency compared to other piggyBac transformation systems.

Another object of the present invention is to provide a transgenic organism that is detectable under ultraviolet light.

A further object of the present invention is to provide a transformation system that includes a vector containing a modified piggyBac sequence, at least one fluorescent protein gene linked to a polyubiquitin promoter, and a helper vector including a heat shock protein gene.

Further objects and advantages of the present invention will become apparent from the following description.

BRIEF DESCRIPTION OF THE DRAWINGS

The patent or application contains at least one drawing executed in color. Copies of this patent or patent application publication with color drawing(s) will be provided by the Office upon request and payment of the necessary fee.

FIG. 1(*b*) is a photograph of a w[m] host strain fly (top) and orange-eye Dm[pBw,gfp] transformant fly (bottom) under brightfield (left) and ultraviolet light (right).

FIG. 1 (c) is a photograph of a w[m] host strain fly (top) and white-eye Dm[pBw, gfp] transformant fly (bottom) under bright field (left) and ultraviolet light (right).

FIG. 2 (b) shows an autoradiogram of a Southern DNA hybridization analysis of Dm[pBw] transformant sublines, and w[m] host strain control samples from transformants using the (experiment I) or phsp-pBac (experiment II) helpers using BglII digestion and Sph/Hpa piggyBac as probe. DNA size markers are shown to the left of the autoradiogram. M (male) and F (female) designations refer to G0 lines, with the numbers below referring to their respective G1 sublines.

FIG. 2 (d) shows a Southern DNA hybridization analysis of Dm[pBw] transformant sublines and w[m] host strain control samples from transformants, using the (experiment I) or phsp-pBac (experiment II) helpers, using NsiI digestion and Nsi/Hpa+Hpa/Nsi probes. DNA size markers are shown to the left of the autoradiogram. M (male) and F (female) designations refer to G0 lines, with the numbers below referring to their respective G1 sublines.

FIG. 3 (d) is an autoradiogram of a Southern DNA hybridization analysis of Dm[pBw, gfp] transformant sublines, and wild type (wt) and w[m] host strain control samples using PstI digestion and Hpa/Ase piggyBac fragment+EGFP DNA as probe. DNA size markers are shown to the left of the autoradiogram. M and F designations refer to G0 lines with specific G1 line numbers are given below, with the designation (+) for those expressing visible eye pigmentation and (−) for those having non-pigmented white eyes.

FIG. 4 (a) is a schematic (not to scale) of the vector insertion in the host plasmid showing the approximate location of the restriction sites and primers used for PCR. Forward (F) and reverse (R) primers are numbered according to their nucleotide position in piggyBac. The piggyBac sequence is shown in gray surrounded by the TTAA (SEQ ID NO 1) duplicated insertion site, the mini-white marker gene is white, and chromosomal sequence is hatched.

FIGS. 6a–6f show SEQ ID NO 6 for pB[PUb-nls-EGFP] #257.

and epifluorescence optics with a Texas red filter (right). A transformant (bottom) is compared to a wild host (top).

Figure 14:
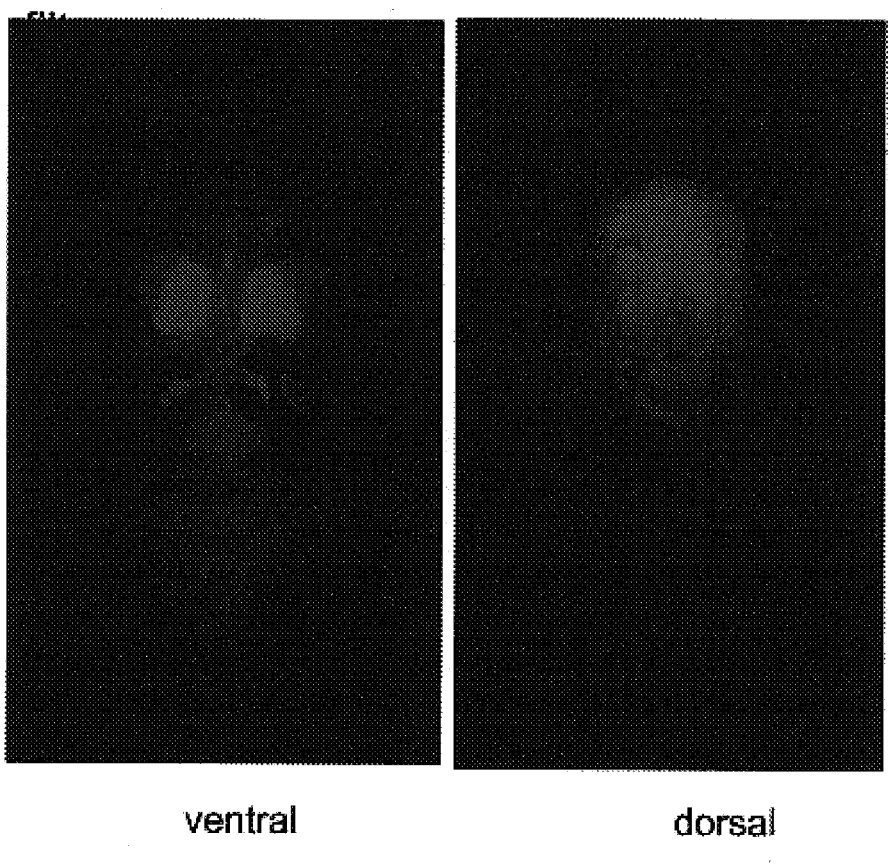

FIG. 14 shows expression of DsRed from the bentral (left) and dorsal (right) view in a Caribbean fruit fly transformed with pB[PUbDsRed] under epifluorescence optics with a Texas red filter.

Figure 15:
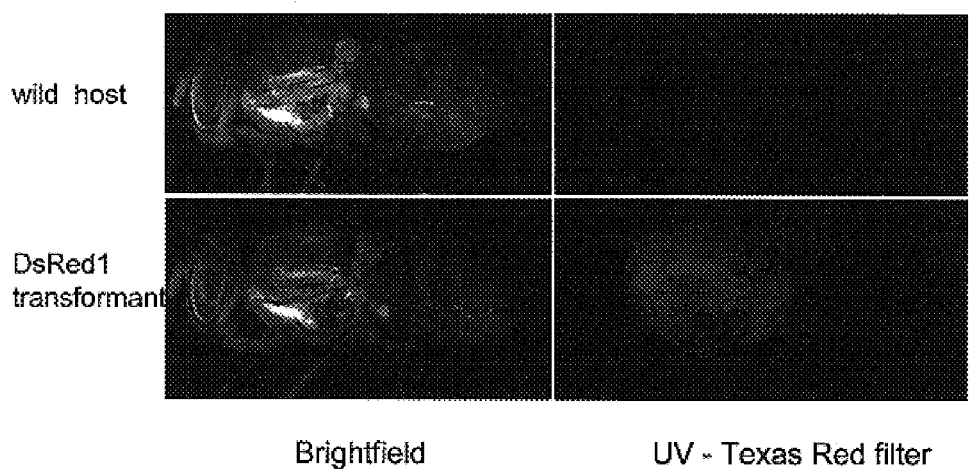

FIG. 15 shows expression of DsRed in a Caribbean Fruit fly transformed with pB[PUbDsRed] under Brightfield (left) and epifluorescence optics with a Texas Red Filter (right). A transformant (bottom) is compared to a wild host (top).

DETAILED DESCRIPTION OF THE INVENTION

The present invention is an effective transformation system for producing transgenic organisms, especially transgenic insects. The identification and isolation of an autonomous piggyBac transposon enables transformation of cells and the production of transgenic organisms wherein DNA capable of being expressed in the transformed cell or transgenic organism is excised from a transformation construct and inserted into the genome of a cell used to produce a transgenic organism (U.S. Pat. No. 6,218,185, issued Apr. 17, 2001; herein incorporated by reference). The term cell for the purposes of this invention includes any cell capable of being transformed by the transformation construct of the present invention, and preferably includes any eukaryotic cell. The term organism for the purposes of the present invention includes any unicellular or multicellular living entity capable of being transformed by the transformation construct of the present invention and preferably includes multicellular eukaryotes. More preferably, the cell or organism is an insect cell or an insect.

The present invention utilizes the transposon machinery of the TTAA (SEQ ID NO 1) specific transposons to excise and insert a targeted functional heterologous DNA sequence into the genome of the host cell. The resulting transformed cell or group of cells are stable transformants that are then used to make a transgenic organism, using techniques known to the skilled artisan, that will pass the introduced gene to all subsequent progeny. The targeted functional heterologous DNA for purposes of this invention is any heterologous DNA capable of being expressed in a host cell and/or a transgenic organism.

Figure 5:
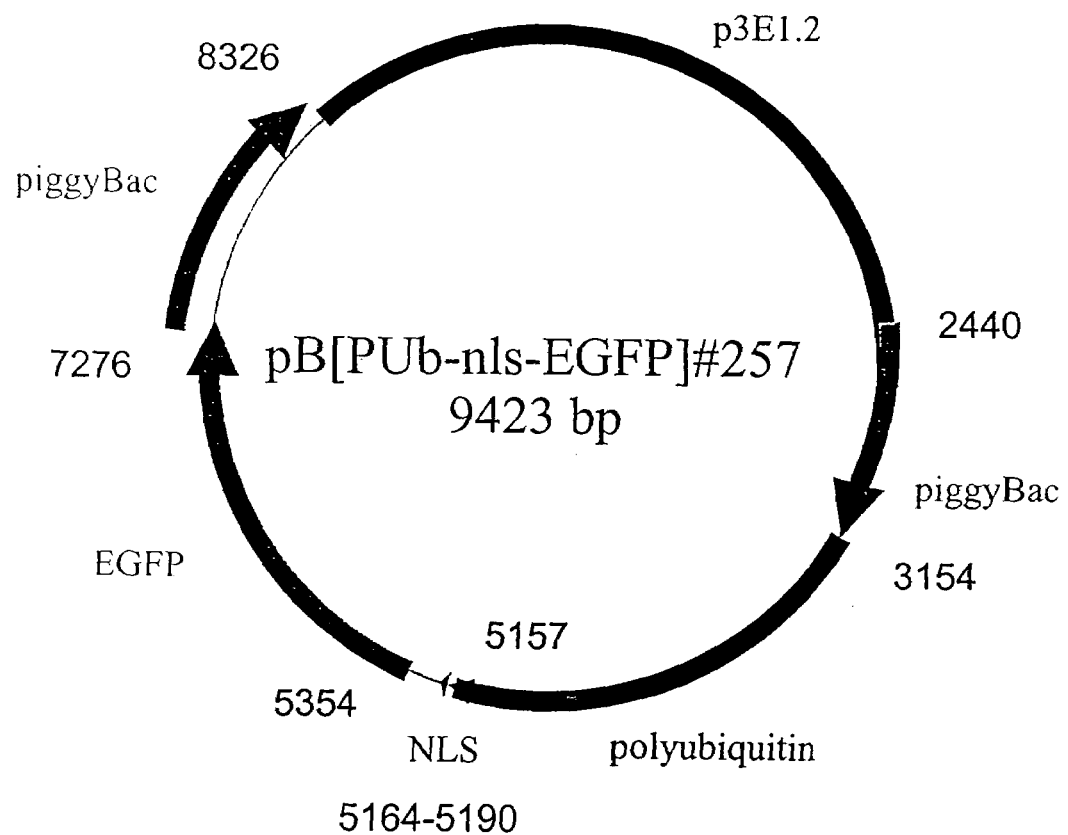
FIG. 5 shows a circular map of the vector pB[PUb-nls-EGFP] #257.
Figure 7A:
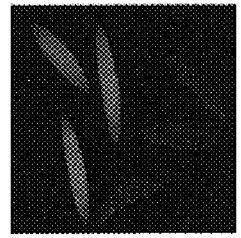
FIG. 7(a) is a photomicrograph showing GFP expression in *Anastrepha suspensa* transformed with piggyBac/PUb-nls-EGFP (pB[PUb-nls-EGFP]) at embryo stages. Under ultraviolet light, transformants exhibit bright green fluorescence, with wild-type non-transformants exhibiting muted yellow autofluourescence (digital images taken with Leica MZ-12 fluorescence microscope and SPOT-1 CCD camera).
Figure 7B:
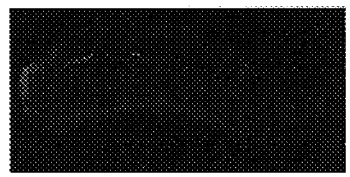
FIGS. 7(b) and 7(c) are photomicrographs showing GFP expression in *Anastrepha suspensa* transformed with pB[PUb-nls-EGFP] at larval stages. 7(b) is a wild-type non-transformant and 7c is a transformant. Under ultraviolet light, transformants exhibit bright green fluorescence, with wild-type non-transformants exhibiting muted yellow autofluourescence (digital images taken with Leica MZ-12 fluorescence microscope and SPOT-1 CCD camera).
Figure 7C:
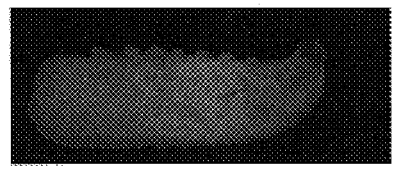
Figure 7D:
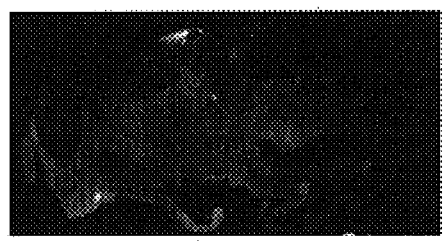
FIGS. 7(d) and 7(e) are photomicrographs showing GFP expression in *Anastrepha suspensa* transformed with pB[PUb-nls-EGFP] at adult stages. 7(d) is a wild-type non-transformant and 7(e) is a transformant. Under ultraviolet light, transformants exhibit bright green fluorescence, with wild-type non-transformants exhibiting muted yellow autofluourescence (digital images taken with Leica MZ-12 fluorescence microscope and SPOT-1 CCD camera).
Figure 7E:
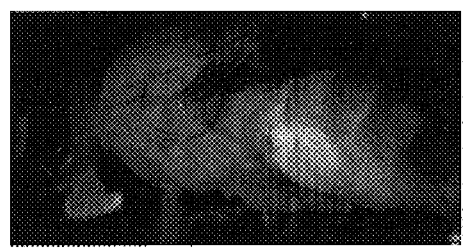
Figure 8A:
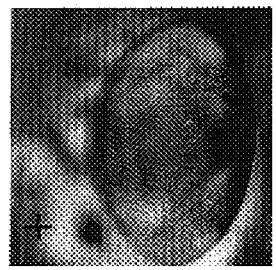
FIGS. 8(a)–8(e) are eye color phenotypes of *Bactrocera dorsalis* wild-type (+) and white eye (WE) host strain and the Bd[pBCcw] transformant lines 61, 115, and 137.
Figure 8B:
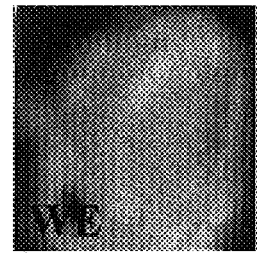
Figure 8C:
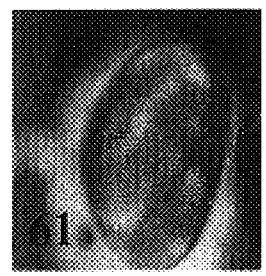
Figure 8D:
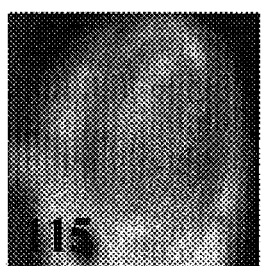
Figure 8E:
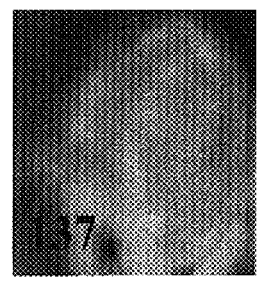
Figure 10:
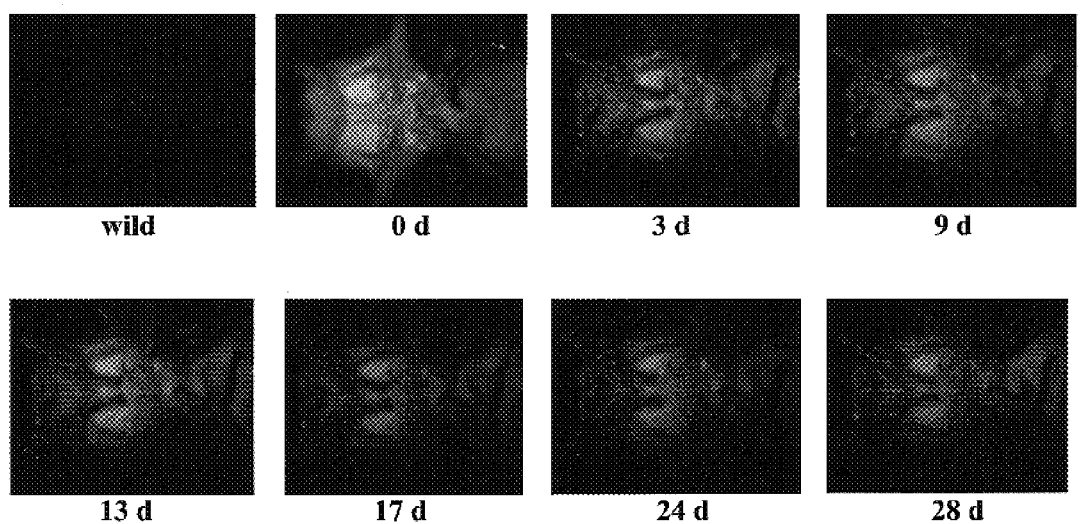
FIG. 10 shows a transgenic insect having three integrations observed under ultraviolet light after various times after decapitation. Flies were decapitated at day 0, taped in a plastic box placed outdoors in partial sunlight. Digital photographs were taken each day at the same exposure and magnification.
Figure 11:
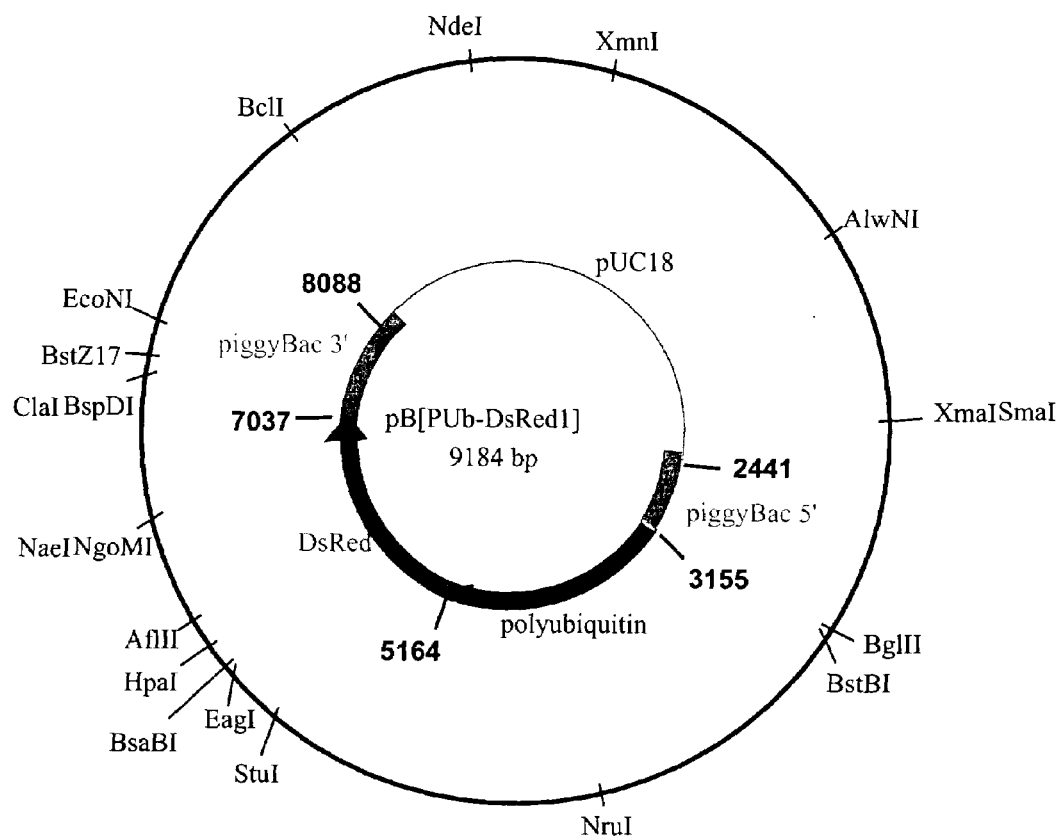
FIG. 11 shows a circular map of pB[PUbDsRed1].
Figure 12:
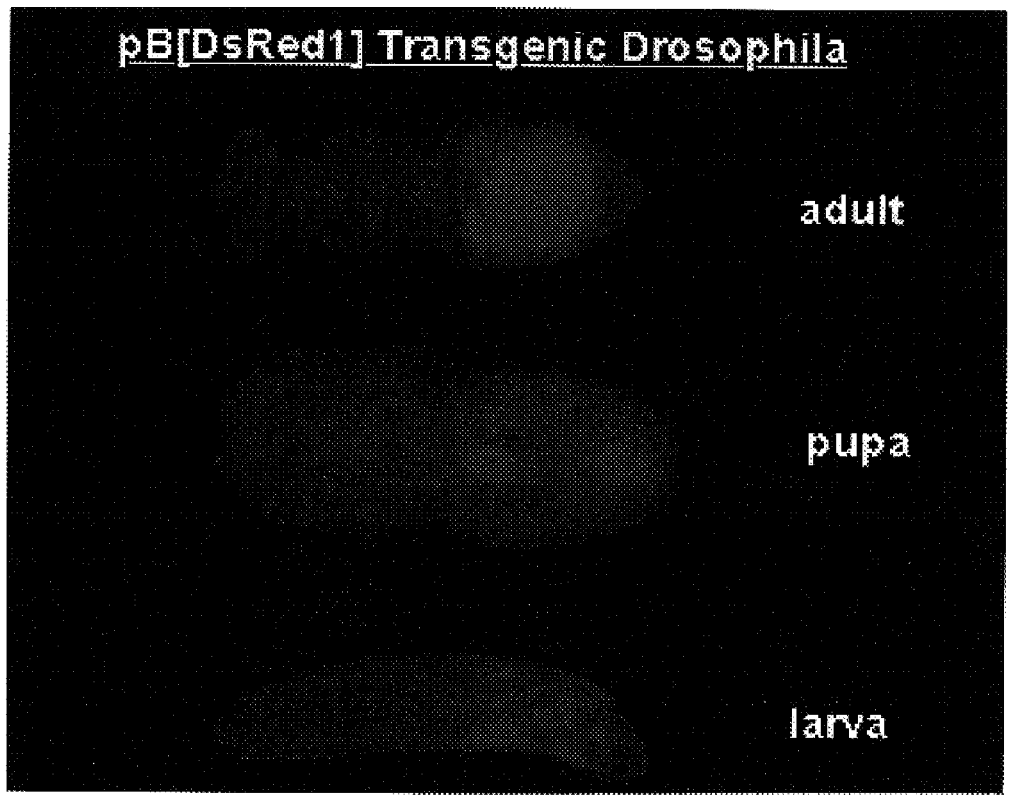
FIG. 12 is a photograph which shows a *Drosophila melanogaster* strain transformed with the pB[PUbDsRed1] vector (piggyBac marked with DsRed1 fluorescent protein gene) at adult (top), pupal (middle) and larval (bottom) stages. Images taken under ultraviolet light with a Texas red filter.
Figure 13:
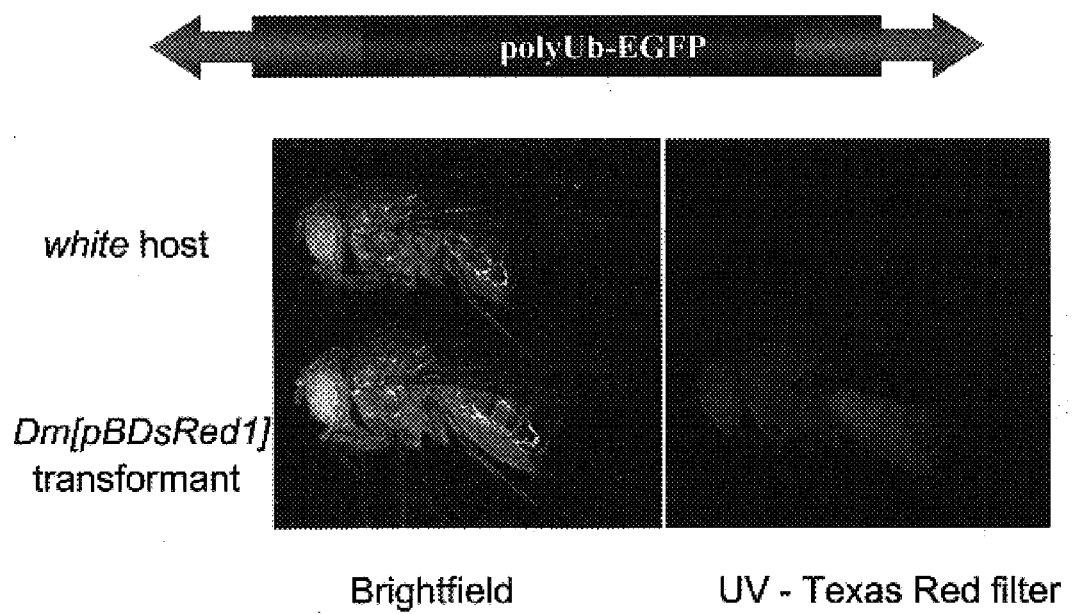
FIG. 13 shows the expression of DsRed in *Drosophila* transformed with pB[PUbDsRed] under Brightfield (left)

The transformation system of the present invention includes a vector, such as, for example, pB[PUb-nls-EGFP], pB[PUbDsRed1], etc. (FIGS. 5, 6, and 11), that includes a modified piggyBac transposon (pB) and a marker construct that includes a fluorescent protein gene under the regulation of a polyubiquitin promoter region. Any fluorescent protein gene capable of being expressed in a transgenic organism is useful in the present invention. Examples of useful fluorescent protein genes are an enhanced green fluorescent protein gene (EGFP), red fluorescent protein gene (DsRed1), blue fluorescent protein gene (BFP), yellow fluorescent protein gene (YFP), cyano fluorescent protein gene (CFP), etc., linked to the promoter region of the *Drosophila melanogaster* polyubiquitin (PUb) gene and the nuclear localizing sequence (nls) of the SV40 virus. These vectors containing at least one fluorescent protein gene, can be used to transform and detect transgenic organisms based on expression of the fluorescent protein marker under ultraviolet light. After chromosomal integration and inheritance of the vector, expression of the fluorescent protein occurs in all cell types and is intense. When the NLS vector is used the expression of the fluorescent protein is strongly localized to nuclei. The fluorescent protein continues to be detectable under ultraviolet light even after death of the organism (FIG. 10). One of the novel features of this vector includes its construction that deletes about 748 bp of internal piggyBac sequence without diminishing its function, and the function of the polyubiquitin promoter in a nondrosophilid species. The vector was created by restriction endonuclease digestion of piggyBac within the p3E1.2 plasmid at the unique BglII site at position 3113 and the unique HpaI site at position 3861. The PUb-nls-fluorescent protein marker cassette was then ligated into the 748 bp deleted region. This has utility as a broadly based method for the creation and selection of transgenic organisms, and as a genetic marker for detecting and tracking transgenic insects used in field release programs (FIG. 5).

Fluorescent protein expressivity is useful for nondrosophilid species not amenable to mutant-rescue, it also widens the possibility for using the dominant expression of flourescent protein as a primary transformant marker in many *Drosophila* lines not already carrying the white or rosy mutations, or for screens requiring selection in early development. Though vectors carrying white and gfp have been tested previously, the transformations used only white as the transformant selection, with GFP assessed secondarily for specific spatial or developmental expression (Davis et al., Devel. Biol., Volume 170, 726–729, 1995; Wang & Hazelrigg, Nature, Volume 369,400–403, 1994).

The transformation system of the present invention also includes a piggyBac transposase helper plasmid, pB ΔSac, having its' 5' terminus deleted as described by Handler et al. (1998, supra; herein incorporated by reference). A new transposase helper under heat-shock promoter regulation was created by the isolation of the 457 bp XbaI-XmnI 5' nontranslated sequence from the hsp70 gene (Lis et al., Cell, Volume 35, 403–410, 1983, herein incorporated by reference). The heat-shock regulated helper increases the transformation frequency by eight-fold in *Drosophila*, indicating that the piggyBac system could be as effective as routinely used systems such as P and hobo that have been thus far inactive in nondrosophilids (O'Brochta & Atkinson, Insect Biochem. Molec. Biol., Volume 26, 739–753, 1996).

The creation of a transformed cell requires that the vector containing the functional heterologous DNA first be physically placed within the host cell. Current transformation procedures utilize a variety of techniques to introduce DNA into a cell. In one form of transformation for vertebrate systems, the DNA is microinjected directly into embryos through the use of micropipettes. Alternatively, high velocity biolistics can be used to propel small DNA associated particles into the cell. In another form, the cell is permeablized by the presence of polyethylene glycol, thus allowing DNA to enter the cell through diffusion. DNA can also be introduced into a cell by fusing protoplasts with other entities that contain DNA. These entities include minicells, cells, lysosomes, or other fusible lipid-surfaced bodies. Electroporation is also an accepted method for introducing DNA into a cell. In this technique, cells are subject to electrical impulses of high field strength that reversibly permeabilizes biomembranes, allowing the entry of exogenous DNA sequences. One method of introducing the transformation system of the present invention into insect embryos, in accordance with the present invention, is to microinject fertilized eggs with the vectors of the present invention. The DNA sequence flanked by the transposon inverted repeats will be inserted into the genome of some of the germ cells of the fertilized egg during development of the organism. This DNA will then be passed on to all of the progeny cells to produce transgenic organisms. The microinjection of eggs to produce transgenic animals has been previously described and utilized to produce transformed mammals and insects (Rubin et al., Science, Volume 218, 384–393, 1982; Hogan et al., Manipulating the Mouse Embryo: A Laboratory Manual, Cold Spring Harbor Laboratory Press, Plainview, N.Y., 1986; Morgan et al., Annu. Rev. Biochem., Volume 62, 191–217, 1993; Spradling, A. C., In: *Drosophila*: A Practical Approach, ed. D. B. Roberts, Oxford: IRL Press, 175–197, 1986; all herein incorporated by reference). Accordingly, a method of producing stably transformed insects includes the step of microinjecting the transformation constructs of the present invention comprising the inverted repeats of a TTAA (SEQ ID NO 1) specific transposon and a helper construct into a cell, preferably a fertile insect egg. This is followed by incubation in an oxygenated and humidified tissue culture chamber at about 22–23° C. for about 3–6 hours. Injected cells or eggs are then heat shocked at about 37°–41° C., about 39° C. preferred, for about 1 hour. The resulting transformed cells or transgenic organisms have exogenous DNA inserted into the genomic DNA at the sequence TTAA (SEQ ID NO 1).

Transformed cells and/or transgenic organisms can be selected from untransformed cells and/or non-transgenic organisms by ultraviolet light since the transformation system includes at least one fluorescent protein gene that produces an altered visible phenotype under ultraviolet light. Using standard techniques known to those familiar with the field, techniques such as, for example, Southern blotting and polymerase chain reaction, DNA can be isolated from transformed cells and/or transgenic insects to confirm that the introduced DNA has been inserted.

Genetic modification of insects with new genetic elements provides a means to control populations of agriculturally pestiferous or beneficial insects. The ability to control pest insects through genetically based sterile insect programs or genetically introduced targeted conditional susceptibilities will result in significant cost savings to agribusiness. This technology can also be used for detection and monitoring of insect populations and infestations where piggyBac transgenic insects are present in the population. In addition, introduction of genes that impart resistance to chemicals (including herbicides, pesticides, and insecticides) can improve the efficacy of beneficial insects. Each of these applications will result in more efficient pest control programs.

Enhancing the resistance of beneficial insects to pesticides will enhance the efficacy of the beneficial insects and may allow for the simultaneous use of chemical control and biological control of pests. Some of the beneficial insects that would make good candidates for such transformations include Hymenopteran parasitoids of *Heliothis* spp.: *Micropilitis croceips* and *Cardiochiles nigriceps*; Hymenopteran parasitoid of Diamondback moth, *Plutella xylostella: Diadegma insolare; Hymenopteran parasitod* of the Indianmeal moth, *Plodia interpunctella: Bracon hebitor*; and Hemipteran predators: *Xylocoris flavipes, Podisus maculatus*.

The following examples are intended only to further illustrate the invention and are not intended to limit the scope of the invention as described by the claims.

EXAMPLE 1

The piggyBac transposase helper plasmid, pBΔSac, having its 5' terminus deleted was described previously (Handler et al., 1998; supra, herein incorporated by reference). pBΔSac was created by digestion of p3E1.2 (U.S. patent application Ser. No. 08/844,274) with SacI and religation, that deletes the 5' piggyBac terminal sequences but maintains the putative piggyBac promoter region. A transposase helper under heat-shock promoter regulation was created by isolation of the 457 bp XbaI-XmnI 5' nontranslated sequence from the hsp70 gene (Lis et al., 1983, supra; herein incorporated by reference). The XbaI-XmnI fragment was blunted and ligated into the SacI-blunted site of pBΔSac to create phsp-pBac. This places the hsp70 promoter sequence upstream of the putative piggyBac promoter.

The pB[Dmw] vector was created by insertion of a *Drosophila melanogaster* mini-white gene (Pirrotta et al., EMBO J., Volume 4, 3501–3508, 1985; herein incorporated by reference) into the 3E1 piggyBac element within the 6.0 kb p3E1.2 plasmid (Cary et al., 1989, supra). The mini-white gene was isolated as a 4.2 kb EcoRI fragment, blunted and ligated into the p3E1.2 HpaI site. The inserted w gene interrupts the piggyBac open reading frame (ORF), but otherwise leaves the piggyBac element intact, with the respective promoters in opposite orientation. A piggyBac vector marked with w and gfp was created by initial construction of piggyBac marked with an enhanced gfp regulated by *D. melanogaster* polyubiquitin (PUb) promoter (Lee et al., Mol. Cell. Biol., Volume 8, 4727–4735, 1988; herein incorporated by reference) linked in-frame to the SV40 nuclear localizing sequence (nls) (Lanford et al., Mol. Cell. Biol., Volume 8, 2722–2729, 1986). The polyubiquitin-nls (PUb-nls) cassette from PUbnlsGFP (Davis et al., 1995, supra) was isolated as KpnI-SmaI fragment and inserted into the KpnI-SmaI cloning site of EGFP-1 (Clontech) (Cormack et al., Gene, Volume 173, 33–38, 1996; Yang et al., Nucleic Acid Res., Volume 24, 4592–4593, 1996). Polyubiquitin-nls-EGFP was then isolated as a 4.1 kb BglII-StuI fragment and ligated into the BglII-HpaI site of piggyBac within p3E1.2 to create pB[PUb-nls-EGFP]. The BglII-HpaI digestion results in a 748 bp deletion within p3E1.2. The mini-white gene was then inserted into the unique BglII site by blunt-end cloning to create pB[Dmw, PUb-nls-EGFP].

EXAMPLE 2

Embryo injections used standard procedures (Rubin & Spradling, Science, Volume 218, 348–353, 1982; herein incorporated by reference) with dechorionation achieved either manually or by 1.6% hypochlorite solution followed by about 2 washings in approximately 0.02% Triton-X 100 in water. Eggs were placed on double-stick tape, desiccated in room-air for about 10–15 minutes and submerged under Halocarbon 700 oil. Injections followed standard *Drosophila* microinjection procedures (Rubin and Spradling, Science, Volume 218, 348–353, 1982; herein incorporated by reference). DNA mixtures had vector:helper concentrations of about 600:400 µg/ml, respectively, in injection buffer (approximately 5 mM KCl; approximately 0.1 mM sodium phosphate; at about pH 6.8). Injected eggs were placed in an oxygenated and humidified tissue culture chamber at about 22–23° C. for about 3–6 hours, and phsp-pBac injected eggs were heat shocked at about 37° C. for about one hour. Hatched larvae were collected about 1–2 days later and placed on larval diet. Eclosed G0 male adults were mated either individually to about 2 or 3 w[m] virgin female adults, or in groups of about three females to about six males. G1 eggs were collected for two weeks and reared under standard conditions that include maintaining the eggs at about 23–25° C. on standard cornmeal-yeast-molasses media (Ashburner et al., supra).

Green fluorescent protein (GFP) was observed at all developmental stages under a Leica MZ-12 stereozoom microscope using a mercury lamp and an epifluorescence longpass filter set (HQ 41012 FITC; Chroma) optimized for red-shifted GFP variants. Photographic documentation used an Olympus OM-4 camera and 400 ASA Fujichrome film with exposure times that were determined empirically.

Figure 1A:
FIG. 1(*a*) is a photograph of eye color phenotypes of Dm[pBw] transformants.

In the first of three transformation experiments, the piggyBac vector system was tested in *D. melanogaster* white strain using a helper transposase under piggyBac regulation (pBΔSac) and a vector marked solely with *D. melanogaster* mini-white gene (pB[Dmw]). A mixture of vector and helper plasmids at concentrations of about 600 and about 400 μg/ml, respectively, was injected into about 2,650 embryos from that about 418 larvae hatched with about 283 emerging as adults. (See Table 1 below). The G0 adults were backcrossed to w[m] flies in groups totaling about 111. Four of the G0 lines yielded G1 offspring having varying levels of eye pigmentation (FIG. 1). One line (F30) was sterile, and one line produced only white eye offspring, and therefore only two of the putative Dm[pBw] transformants were verified. One of these (F13) exhibited eye pigmentation only in females in several succeeding generations, suggesting that the integration caused a sex-linked lethal mutation. Presuming a fertility rate of about 50% (fertility rates are typically between about 40–60%; see below), an approximate transformation frequency of about 1–3% of fertile G0s was obtained.

In a second experiment, the pB[Dmw] vector was again tested but with a piggyBac transposase helper under *D. melanogaster* hsp70 (Lis et al., 1983 supra) promoter regulation (phsp-pBac). A vector/helper mixture, at a concentration of approximately 600/400 μg/ml was injected into about 1,940 embryos, of which about 247 larvae hatched, with about 122 emerging as adults (See Table 1, below). G0 adults were initially backcrossed in a total of about 49 groups to w[m] flies, after which they were individually mated to determine fertility. Of the about 98 surviving G0 flies, about 41 yielded offspring resulting in a fertility rate of about 42%. Of the 41 fertile G0 flies, 11 lines produced offspring having varying levels of eye coloration (FIG. 1) yielding a transformation frequency of about 26%. The number of G1 offspring from the G0 lines varied considerably, ranging from 1 G1 in lines M11 and F1, to 102 G1 flies in line M13.

Figure 1B:
Figure 1C:

In a third experiment, the phsp-pBac helper was used, but with a piggyBac vector including the enhanced green fluorescent protein (gfp) marker gene in addition to the *D. melanogaster* white gene. This allowed the testing of a new gfp marker construct in transformants that could be primarily identified by white expression. Although expression of wild type GFP under polyubiquitin-nuclear localizing sequence regulation had been tested previously in *D. melanogaster* P transformants (Davis et al., 1995, supra), the vector of the present invention improves expression of GFP by using an enhanced GFP (EGFP-1) having a double mutation causing a reported increase in expression of up to about 35-fold (Cormack et al., 1996, supra; Yang et al., 1996, supra). The variant form is also optimized for mammalian codon usage and polyadenylation, and preliminary tests of the marker construct indicated transient GFP expression in both *Drosophila* embryos and dipteran and lepidopteran cell lines (A. M. Handler and R. A. Harrell, unpublished). The vector construct, pB[Dmw, PUb-nls-EGFP], also allowed evaluation of piggyBac transformation with about a 10.0 kb vector, approximately 3.4 kb larger than previous vectors tested, and having about 748 bp of piggyBac DNA deleted (previous vectors retained all piggyBac DNA). As before, a mixture of about 600 μg/ml vector and about 400 μg/ml helper was injected into about 2147 embryos, of which about 412 larvae hatched, and about 218 emerged as adults (Table 1 below). G0 adults were backcrossed to w[m] flies in a total of about 90 mating groups, of which about 79 yielded offspring. Although white+gene expression (eye pigmentation) was depended upon as the primary marker, G1 larvae and pupae were examined under ultraviolet light for visible GFP expression, and seven of the G0 lines yielded fluorescent G1 larvae and pupae. Interestingly, as shown below in Table 2, upon adult emergence only six of the seven G0 lines yielded G1 offspring with observable eye color pigmentation. While about 70 G1 offspring in total exhibited observable green fluorescence, only about 27 of these flies exhibited a level of eye pigmentation that would have allowed their selection under normal screening procedures. In contrast, all of the G1 flies with eye color pigmentation expressed GFP. FIG. 1b shows a Dm[pBw, egfp] transformant having an orange eye color and GFP fluorescence, with no fluorescence observed in the w[m] host. FIG. 1c shows another transformant having a white eye phenotype indistinguishable from that in the w[m] host strain, but exhibiting an equal, if not greater level of GFP fluorescence compared to the orange eye transformant. Notably, fluorescence is quenched in the eye of the pigmented transformant, while it is easily visible in the white eye transformant. High magnification examination revealed a few pigmented ommatidia in some white eye G1 flies expressing GFP, though these would not have been normally detected. Based on selection by GFP expression and presuming about 50% fertility, an approximate transformation frequency of about 6–7% of fertile G0 flies is deduced.

An assessment of vector activity based on germline transformation frequency is a factor of both transposon mobility in the host embryo and levels of genomic position effect suppression of the marker gene, or stated more simply, the ability to visibly identify putative transformants. While position effect variegation and suppression of white expression in transformants is well established (Hazelrigg et al., Cell, Volume 64, 1083–1092, 1984; Pirrotta et al., 1985, supra), the effect of complete marker suppression on transformation frequencies has not been assessed since such transformants have been only detected fortuitously after molecular analysis. The experiment using both the white and GFP markers proved the importance of position effects on marker expression convincingly, since GFP was readily detectable in 70 G1 flies, yet eye pigmentation was apparent in less than 40% of these. Under typical screening procedures these flies would not have been scored as transformants, though pigmentation in a few ommatidia in some flies could be detected at high magnification, and for a few lines, pigmentation was more apparent in subsequent generations. It is likely that expression of the white marker would have been improved by heat shock regulation, but nonetheless, GFP was easily detected in all the non-pigmented transformants, and strongly expressed in some. The influence of modifier genes on position effect variegation is complex, and target genes (or their promoters) are not equivalently affected (Bhadra et al., Genetics, Volume 150, 251–263, 1998). The polyubiquitin-gfp gene may be a target of position effect modifiers, but it is clearly less susceptible to suppression relative to white in terms of its expressed phenotype in the same chromosomal context. The data suggests that GFP is a more reliable visible marker than white, that portends well for its use as a general marker in other insects.

EXAMPLE 3

Southern hybridization was performed to verify genomic transposition of the piggyBac vectors. Approximately 5–10 μg of genomic DNA was digested with indicated restriction enzymes and separated on about 0.8% agarose gels. DNA was stained with ethidium bromide, blotted to nylon filters and immobilized by ultraviolet irradiation. Hybridization probes were labeled with [$^{32}$P]-dCTP by random priming (Gibco BRL) according to the manufacturer's specifications. Probe DNA was generated from indicated piggyBac restriction fragments (see below) that were separated from p3E1.2, or the entire egfp gene from pEGFP-1 (Clontech) by agarose electrophoresis and gel-elution. Hybridizations were performed in phosphate buffer, approximately pH 7.5; about 1% BSA; about 7% SDS at about 65° C. with an initial wash in about 2×SSC; about 0.2% SDS at about room temperature and about two washes in about 1×SSC; about 0.1% SDS at about 55° C. for approximately 30 minutes. Autoradiography was performed by exposure of Kodak X-Omat film at about −90° C.

Genomic transposition of the piggyBac vectors was verified by Southern DNA hybridization. The basic strategy was to perform hybridizations to the 5' vector arm using the piggyBac SphI-HpaI or NsiI-HpaI fragment as probe, and the 3' vector arm using the HpaI-AseI or HpaI-NsiI fragment as probe. Using probes to both vector arms, internal fragments spanning most of the vector were detected. Hybridizations to the vector arms and adjacent chromosomal sequence indicate their presence in non-plasmid DNA and indicate the number of integrations, while internal hybridizations that yield known fragment sizes confirm vector integrity.

Figure 2A:
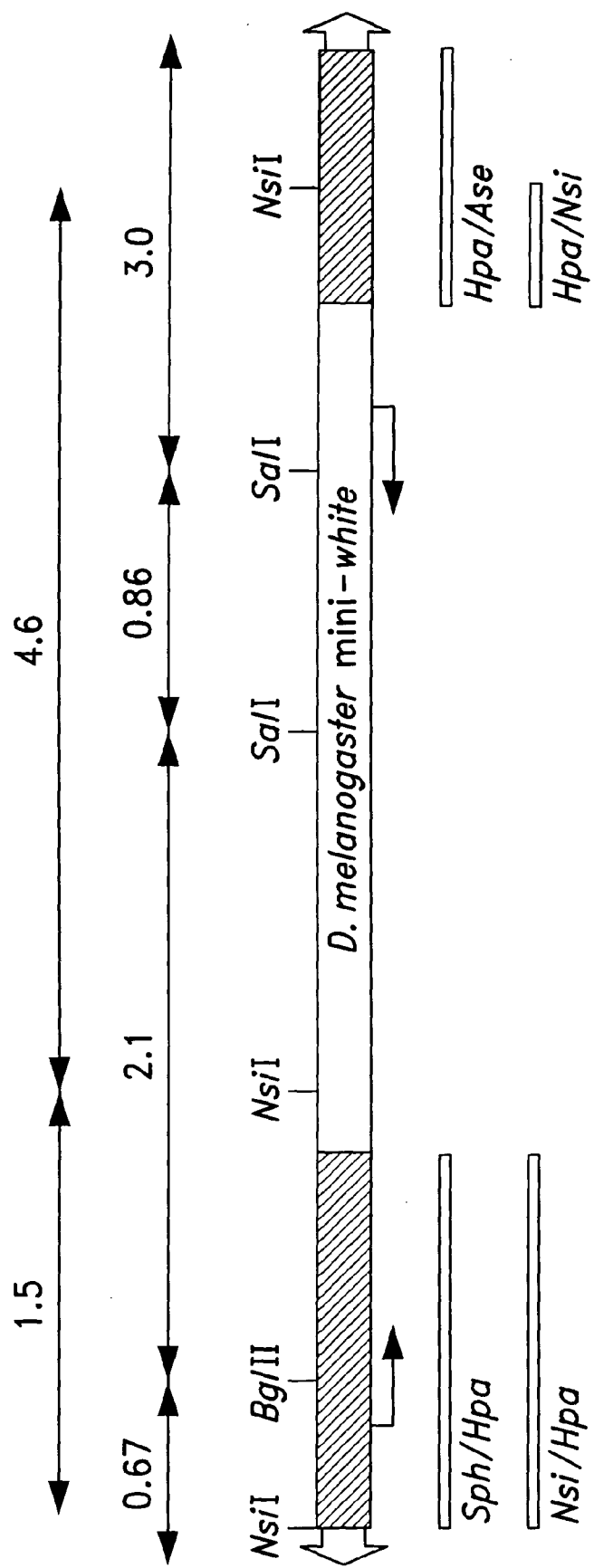
FIG. 2 (a) is a schematic (not to scale) of the pB[Dmw] vector showing the BglII, SalI, and NsiI restriction sites used to digest the genomic DNA, and the probes used for hybridization (bars). Above the schematic are distances in kilobases used to calculate internal restriction fragment sizes and minimum sizes for junction fragments. PiggyBac vector sequences are shaded gray, and the mini-white marker gene is white.
FIG. 2(c) shows a Southern DNA hybridization analysis of Dm[pBw] transformant sublines and w[m] host strain control samples from transformants, using the (experiment I) or phsp-pBac (experiment II) helpers, using SalI digestion and Hpa/Ase piggyBac as probe. DNA size markers are shown to the left of the autoradiogram. M (male) and F (female) designations refer to G0 lines, with the numbers below referring to their respective G1 sublines.

For pB[Dmw] transformants, genomic DNA was initially digested with BglII and hybridized to the labeled Sph-Hpa piggyBac fragment, that detects both vector arms resulting in two bands for each integration (FIG. 2A). Each intact vector integration should result in one band greater than about 0.67 kb for the 5' arm, and one band greater than about 5.9 kb for the 3' arm. Since varying eye color phenotypes among G1 sublines was observed, and in some cases within G1 sublines, sublines having light orange, dark orange, or red eye coloration from the same G1 sublines were selected for hybridization analysis. For example, flies having differing phenotypes from lines M13-39, M19-90, and M19-91 were hybridized separately, but no difference in the number or sites of insertion were apparent. Of all the lines tested, all had single integrations except for two lines having two integrations (M13-39 and M19-91) and one line having three integrations (F14-63). All the lines with multiple integrations had dark orange or red eye color, though several lines with a single integration also shared these phenotypes. Hybridization patterns for the lines tested indicated that for most of the G0 lines, different integrations were transmitted to many of the G1 sibling offspring. For example, the three G1 sublines tested from both the M3 and M5 G0 lines all show different patterns indicating at least three independent integrations occurring in the two G0 germlines.

Figure 2B:
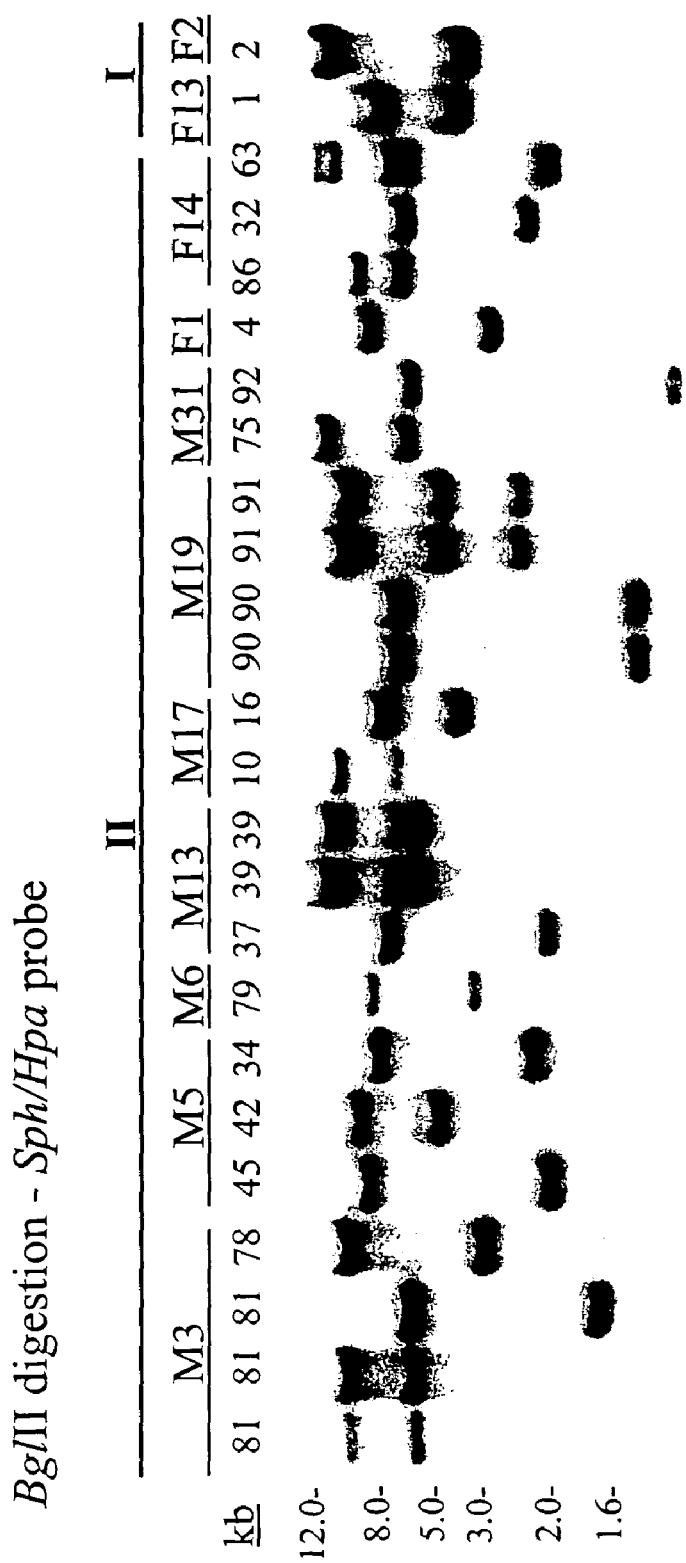
Figure 2C:
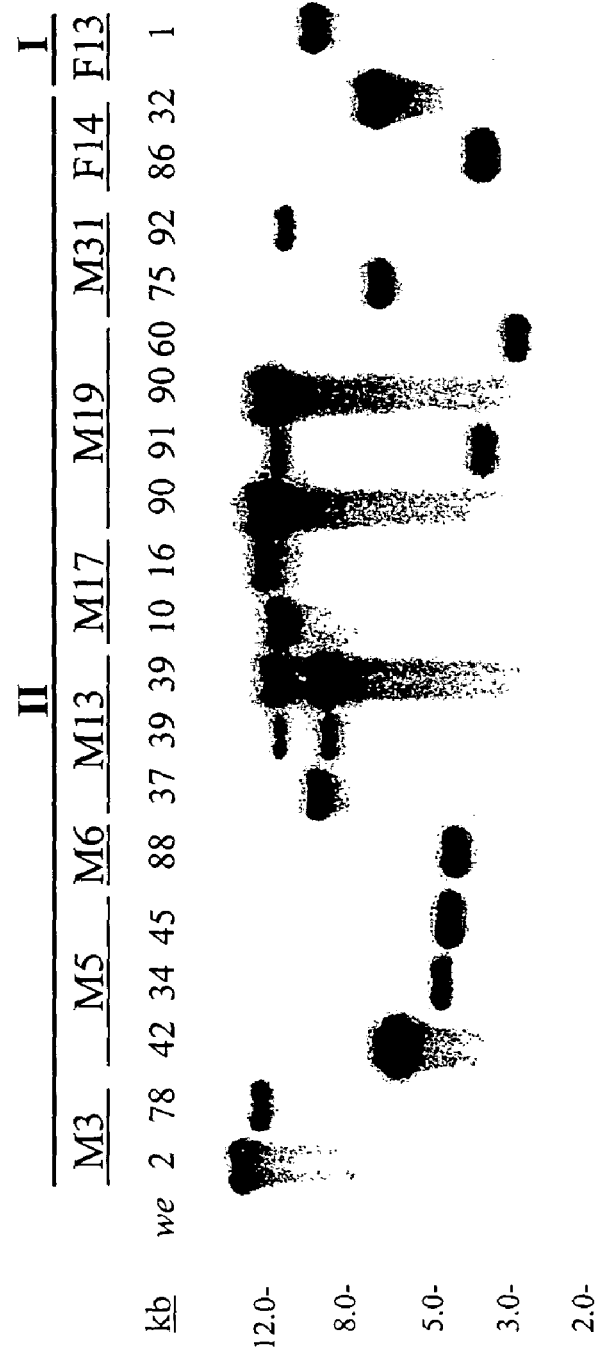
Figure 2D:
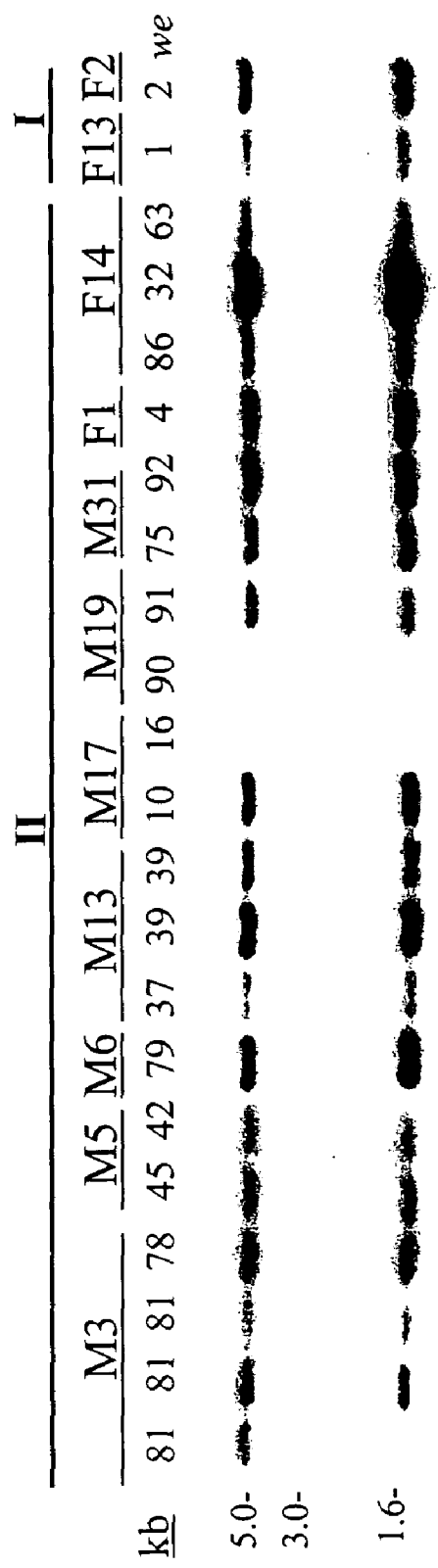

Genomic DNA digested with SalI and hybridized to HpaI-AseI probe yielded single bands greater than about 3.0 kb for each integration, and the number of integrations determined were consistent with the SphI-HpaI hybridizations (FIG. 2B). For all samples, NsiI digestion and hybridization to Nsi-HpaI and HpaI-NsiI probe yielded only about 1.5 kb and about 4.6 kb bands accounting for about 6.1 kb of the about 6.6 kb vector, indicating the same generally high level of vector integrity for all integrations tested.

Figure 3A:
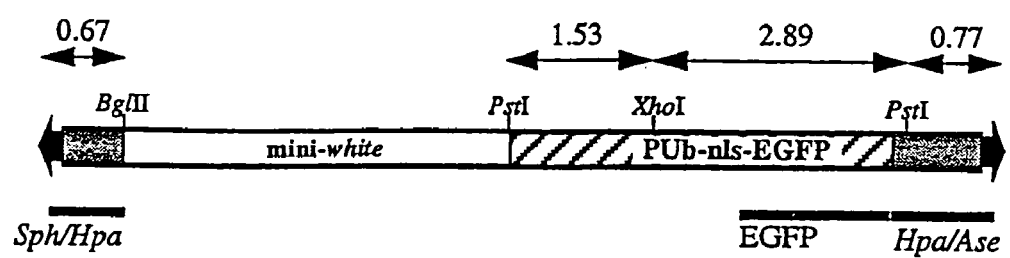
FIG. 3(a) is a schematic (not to scale) of the pB[Dmw, PUb-nls-EGFP] vector showing the BglII, XhoI, and PstI restriction sites used to digest the genomic DNA, and the probes used for hybridization (bars). The Sph/Hpa piggyBac as probe contains 0.67 kb of vector sequence (SphI to BglII) with BglII to HpaI piggyBac sequence deleted from the vector. Above the schematic are distances in kilobases used to calculate internal restriction fragment sizes and minimum sizes for junction fragments. PiggyBac vector sequences are shaded gray, the mini-white marker gene is white, and the EGFP marker gene is hatched.
Figures 3B, 3C:
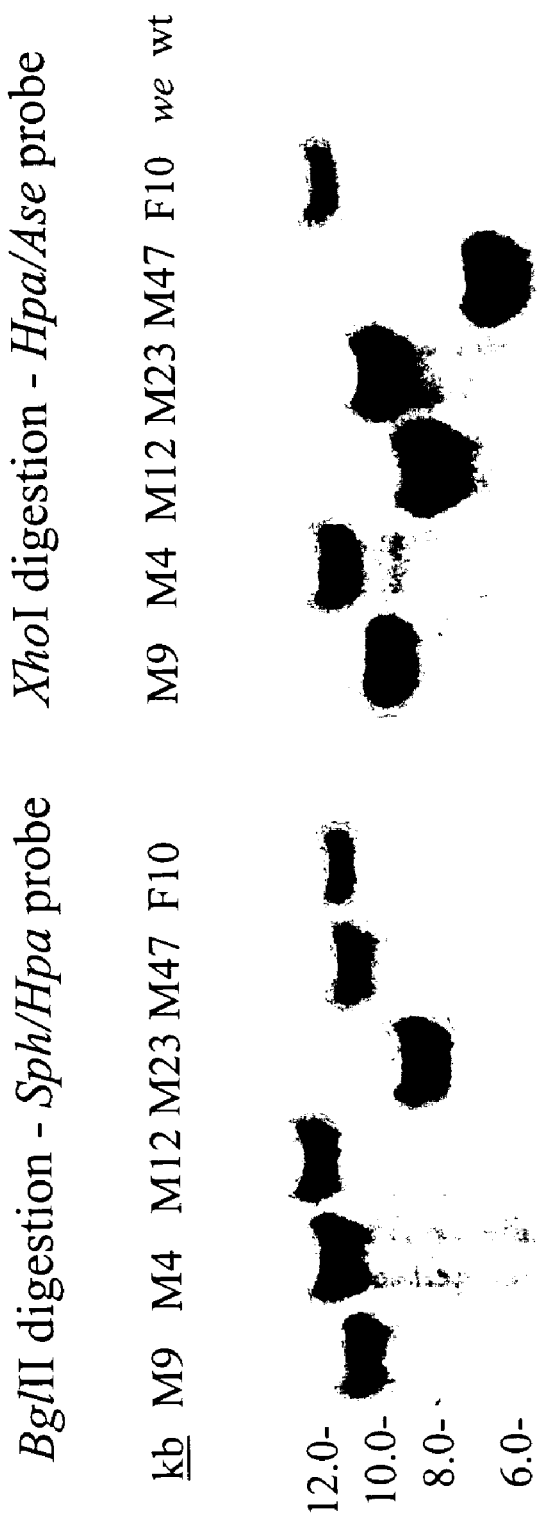
FIG. 3(b) is an autoradiogram of a Southern DNA hybridization analysis of Dm[pBw, gfp] transformant sublines, and wild type (wt) and w[m] host strain control samples using BglII digestion and Sph/Hpa piggyBac as probe. DNA size markers are shown to the left of the autoradiogram. M (male) and F (female) designations refer to G0 lines with selected G1 transformant progeny of samples.
Figure 3D:
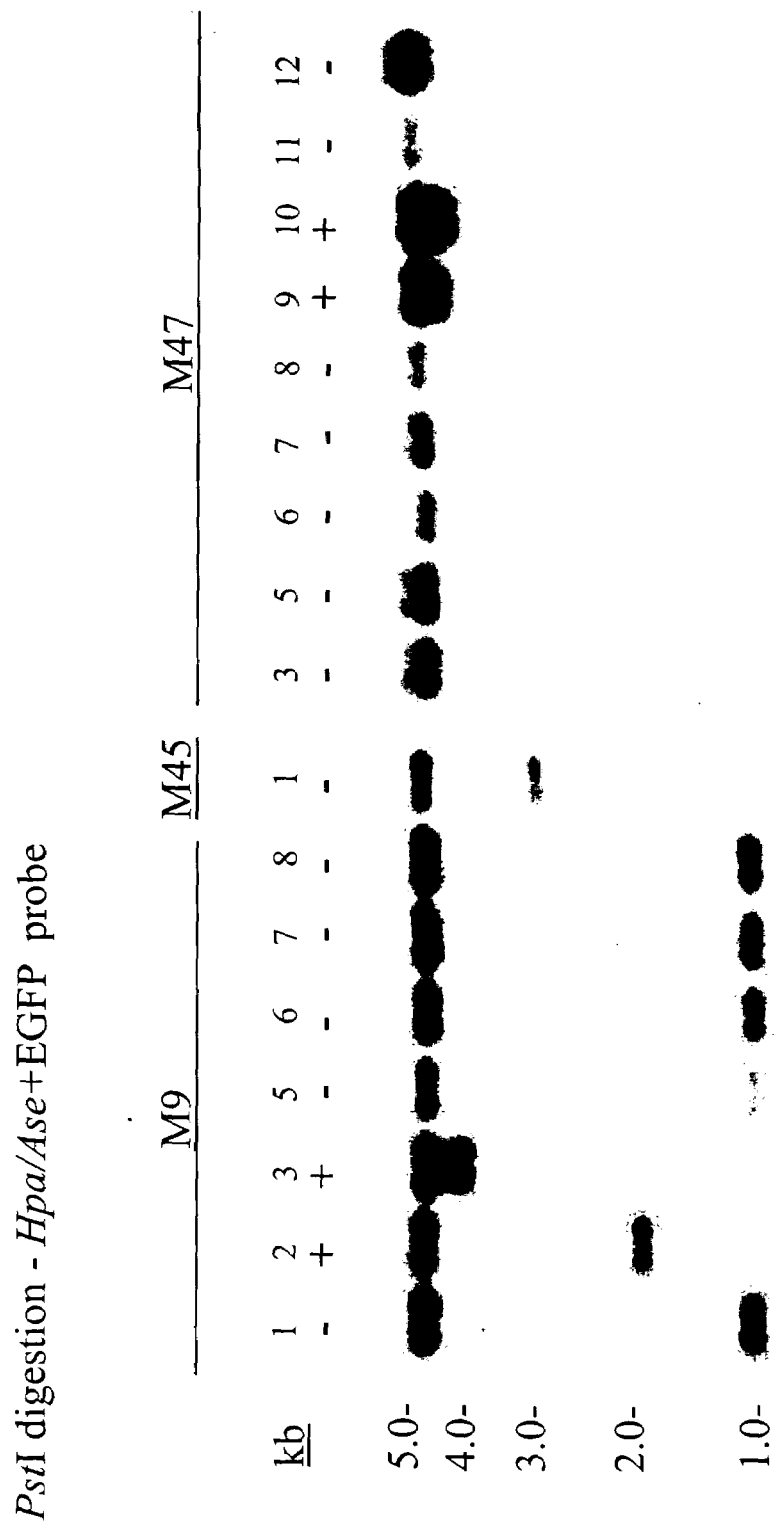
FIG. 3 (c) is an autoradiogram of a Southern DNA hybridization analysis of Dm[pBw, gfp] transformant sublines, and wild type (wt) and w[m] host strain control samples using XhoI digestion and Hpa/Ase piggyBac fragment as probe. DNA size markers are shown to the left of the autoradiogram. M and F designations refer to G0 lines with selected G1 transformant progeny of samples.

G1 sublines from six G0 lines transformed with the pB[Dmw, PUb-nls-EGFP] vector were digested with either BglII and probed with SphI-HpaI piggyBac DNA for 5' vector arm analysis, or digested with XhoI and probed with HpaI-AseI piggyBac DNA for 3' arm analysis (FIGS. 3A and 3B). Both hybridizations yielded one band for each sample, indicating single integrations having occurred in each line. NsiI restriction digests with NsiI-HpaI and HpaI-NsiI hybridizations yielded about 0.7 kb and about 0.8 kb bands indicating vector integrity for each integration (data not shown).

Two G0 lines, M9 and M47, yielded a high proportion of G1 flies expressing only GFP and white eyes, and line M45 that yielded only white eye transformants. These lines were analyzed by PstI digestion and hybridization to EGFP and Hpa-Ase. All lines shared the about 4.4 kb internal vector fragment, with an additional junction fragment from the 3' vector arm and adjacent insertion site chromosomal DNA. The M9 white eye lines all shared the same integration indicated by an about 0.9 kb junction fragment, and similarly the M47 white eye lines all shared the same 5.0 kb junction fragment. The pigmented lines M9-2 and M9-3 had different integrations from each other, and from their white eye sibling lines, and the pigmented lines M47-9 and M47-10 shared the same integration based on an about 4.0 kb junction fragment, but which differs from their white eye siblings. These hybridizations, and that for M45-1, proves that the white eye flies were transformed, and that white expression was likely influenced by differing insertion sites from their pigmented sibling lines.

EXAMPLE 4

Figure 4A:
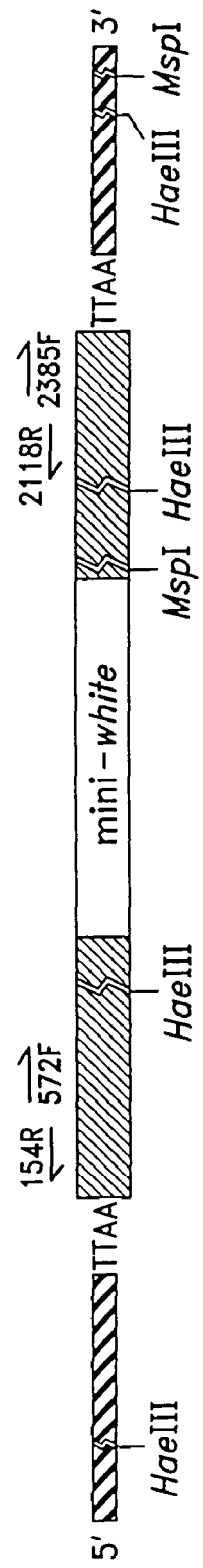
FIGS. 4 (a) and (b) show inverse PCR strategy to isolate the pB[Dmw] vector insertion site in transformant sublines.
FIG. 4(b) shows the piggyBac insertion site sequence in p3E1.2 (SEQ ID NOs 7 and 8), and the proximal insertion site sequences (SEQ ID NOs 9 and 10, 11 and 12, and 13 and 14) for three of the transformant sublines.

To verify that piggyBac-mediated chromosomal transpositions had occurred, insertion sites were isolated by inverse PCR from sublines F1-2, M17-4 and M31-6, all having single integrations. Inverse PCR was performed as described previously (Handler et al., 1998, supra; herein incorporated by reference) using HaeIII digestions for 5' and 3' junctions and MspI digestion for 3' junctions. After about 4 hours digestion, restriction fragments were circularized by ligation at about 16° C. for about 16 hours. PCR was preformed on the circularized fragments by using primer sequences in opposite orientation within the piggyBac restriction site and terminus for each junction. For the 5' junction, the forward primer (572F) 5'-TCTTGACCTTGCCACAGAGG-3' (SEQ ID NO 2) and reverse primer (154R) 5'-TGACACTTACCGCATTGACA-3' (SEQ ID NO 3) were used. For the 3' junction the reverse primer (2118R) 5'-GTCAGTCCAGAAACAACTTTGGC-3' (SEQ ID NO 4) and the forward primer (2385F) 5'-CCTCGATATACAGACCGATAAAAACACATG-3' (SEQ ID NO 5) were used. PCR products were separated in low-melting-temperature agarose, and fragments were selected that were longer than the respective restriction site terminus distances and different from those expected from the p3E1.2 based vector and helper plasmids. These products were directly subcloned into ddT vectors (Invitrogen), that were sequenced by using primers to vector sequence proximal to the respective termini. Subcloned PCR products were sequenced and analyzed by alignment using GeneWorks 2.5 software (Oxford Molecular Group) and subjected to BLAST analysis (Altshul et al., J. Mol. Biol., Volume 215, 403–410, 1990; herein incorporated by reference) to identify genomic insertion site sequences and distinguish them from those in the injected plasmids. For all the integrations both the 5' and 3' junctions yielded the piggyBac inverted terminal repeat sequences immediately adjacent to a TTAA sequence (SEQ ID NO 1) and proximal insertion site DNA (FIG. 4). The TTAA (SEQ ID NO 1) duplicated target site is characteristic of all piggyBac integrations (Elick et al., Genetica, Volume 97, 127–139, 1995) and typically indicates a vector-mediated transposition. The BLAST analysis revealed that the M17-4 integration occurred in a TTAA site within the cubitus interruptus-Dominant gene located on chromosome 4 at nucleotide 12,898 (GenBank submission U66884; Ahmed & Podemski, Gene, Volume 197, 367–373, 1997), and the M3106 integration was found to have occurred in a TTAA site within a previously sequenced region of the distal X chromosome (GenBank submission AL09193; Murphy et al, direct submission). Determination of insertions in these previously sequenced sites gives the first direct proof that a piggyBac vector does indeed insert into and duplicates TTAA (SEQ ID NO 1) insertion sites in a eukaryotic genome.

Two of the three insertion sites that were sequenced were found to be in previously sequenced genomic loci, and as expected, the insertions sites were all TTAA (SEQ ID NO 1) with one of them within the $ci^D$ allele on the fourth chromosome. Many transposons have insertion site preferences, and for at least some, a clear negative bias against specific sites or loci. This has been clearly demonstrated by genomic hotspots and coldspots for P integration in *D. melanogaster* (See Engels, In: *Mobile DNA*, D. E. Berg and M. M. Howe, eds., American Society of Microbiology, Washington, D.C., 439–484, 1989), and by differences in preferential integration sites between hobo and P (Smith et al., Genetics, Volume 135, 1063–1076, 1993). If the TTAA (SEQ ID NO 1) specificity for piggyBac integration is not further influenced by proximal sequences, then piggyBac transpositions may find use in transposon-mutagenesis and enhancer traps for loci refractory to P or hobo transpositions in *Drosophila*.

EXAMPLE 5

The Caribbean fruit fly, *Anastrepha suspensa*, was transformed with a piggyBac vector marked solely with PUb-nls-GFP(pB[PUb-nls-EGFP]) (FIGS. 5 and 6) using the hsp70-piggyBac (phsp-pBac) helper. From injected embryos, 561 surviving G0 adults were intermated in 60 small groups. Four of the G0 groups yielded a total of 57 G1 offspring exhibiting green fluorescence at all stages of development (See FIG. 7) and chromosomal vector integrations were verified by Southern hybridization for each G0 group. To test GFP as a genetic marker for field released transgenic flies, the perdurance of GFP expression was assayed in transgenic flies killed by decapitation. Two to three day old *A. suspensa* adults transformed with pB[PUb-nls-EGFP], and wild type non-transformed adults, were decapitated and placed within a plastic box kept outdoors in partial shade. GFP fluorescence was observed daily by digital images taken with a SPOT-1 cooled CCD digital camera (Diagnostic Instruments, Inc.) through a Leica MZ-12 stereozoom microscope. All images were taken at the same magnification and exposure parameters. FIG. 10 shows that while GFP fluorescence decreases with time after death, unambiguous detection of GFP is still possible at 28 days after decapitation, with no fluorescence detectable in wild flies (FIG. 10). This indicates that the PUb-nls-EGFP marker should be a reliable visible detection system for released transgenic insects, and especially for those captured and killed in field traps with monitoring occurring after extended time periods.

EXAMPLE 6

A piggyBac vector marked with the Mediterranean fruit fly (*Ceratitis capitata*) white gene cDNA (pB[Ccw]) and the phsp-pBac helper was used to transform the oriental fruit fly (*Bactrocera dorsalis*). Injected G0 embryos from the *B. dorsalis* white eye mutant strain yielded 102 fertile adults, that upon individual backcrossing, yielded three lines of putative transformants with pigmented eyes (FIGS. 8a–8e). One of these lines produced 119 G1 transformants. Southern DNA hybridization analysis with piggyBac and white gene probe verified chromosomal integration of the piggyBac-white vector in all three lines. In a separate experiment, the white/PUb-nls-EGFP marker within pB[Ccw, PUb-nls-EGFP] was introduced into a single *B. dorsalis* transformant line from 17 G0 matings. As in *Drosophila*, the transformant was selected solely by GFP expression, having undetectable eye coloration. This reaffirms the notion that the polyubiquitin-EGFP marker is significantly more reliable than white gene markers.

EXAMPLE 7

Figure 9A:
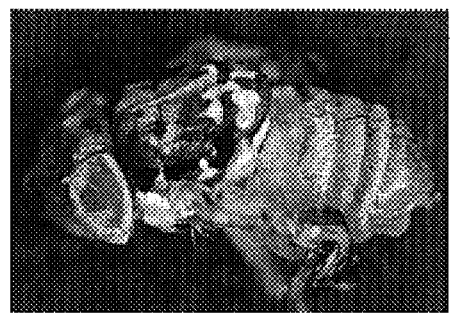
FIGS. 9(a) and 9(b) show medfly, *Ceratitis capitata* transformed with piggyBac/white/EGFP vector (pB[Ccw, pUB-nls-EGFP]) expressing eye color under brightfield (9a) and GFP expression under ultraviolet light (9b).
Figure 9B:

The PUb-nls-EGFP marker was introduced into the medfly, *Ceratitis capitata*, to further test GFP as a transgenic selection, and to create GFP-marked strains for testing as a field release marker in medfly SIT. First a piggyBac vector marked with PUb-nls-GFP and the medfly white gene (pB [Ccw, PUb-nls-EGFP]) was tested, and then the vector solely marked with PUb-nls-GFP pB[PUb-nls-EGFP]) was tested. Both experiments used the hsp70-piggyBac (phsp-pBac) helper. Based on GFP fluorescence, the first experiment yielded five transformant lines from 99 fertile G0s (See FIG. 9), while the second experiment yielded three transformed lines from 17 fertile G0s. Transformation was verified by Southern hybridization analysis.

EXAMPLE 8

The plasmid pB[PUbDsRed1] piggyBac vector marked with polyubiquitin-regulated DsRed1 (Matz et al., Nat. Biotechnol., Volume 17, 969–973, 1999; herein incorporated by reference) was created by isolating the polyubiquitin promoter (Lee et al., Mol. Cell. Biol., Volume 8, 4727–4735, 1988; herein incorporated by reference) as an EcoRI-BglII fragment from PUbnlsGFP (Davis et al., 1994, supra;) and ligating it into the EcoRI-BglII N-terminal cloning site of pDs-Red1-N1 (Clontech, Palo Alto, Calif.), creating pPUbDsRed1. The polyubiquitin-DsRed 1 gene was isolated as a BglII-NotI fragment that was used to replace the PUb-nls-EGFP-1 marker cassette within the BglII-NotI site of pB[PUb-nls-EGFP] (Handler and Harrell, Insect Mol. Biol., Volume 8, 449–458, 1999; herein incorporated by reference). Construction of the hsp70-regulated transposase helper, phspBac, was as described in Handler and Harrell (supra).

The pB[hsp-GAL4, EGFP] vector was created by ligating the hsp70-GAL4 cassette, from pF89 (Brand et al., Development, Volume 118, 401–415, 1993; herein incorporated by reference) as a BglII-StuI fragment, into the BglII and blunted BstBI site of pB[PUb-nls-EGFP]. The pB[UAS-DsRed1, EGFP] vector was created by isolating DsRed1 from pDsRed1–N1 as a BamHI/NotI fragment and ligating it into the BglII/NotI sites of PUAST (Brand et al, supra) to create pUAS-DsRed1. The UAS-DsRed1 fragment from PUAS-DsRed1 was then isolated as a BamHI fragment and ligated into the BglII site of pB[PUb-nls-EGFP].

EXAMPLE 9

Fluorescent protein expression was observed at various developmental stages from transgenic insects having single integrations of DsRed or EGFP as determined by Southern analysis. Fluorescence was observed under a Leica MZ-12 stereozoom fluorescent microscope using a mercury lamp and appropriate filter sets (Chroma Technology Corp., Brattleboro, Vt.). For DsRed detection the HQ Texas Red™ set #41004 was used having the following filters: exciter HQ560/55x; dichoric Q595LP; emission HQ645/75m. For EGFP detection the FITC/RSGFP LP Emission set #HQ 41012 was used having the following filters: exciter HQ480/40; dichroic Q505LP; emission HQ510LP. Digital images were obtained with a SPOT-1 cooled CCD camera (Diagnostic Instruments, Sterling Heights, Mich.) and captured with Adobe Photoshop 4.0 software (Adobe Systems Inc., San Jose, Calif.). For comparison fo fluorescent protein expression automatic exposures were calculated and images taken for each protein from a transformed adult using the appropriate filter set. These settings were also used as a user-defined exposure for the other protein.

EXAMPLE 10

Germ-line transformation was tested in the white mutant strain, w[m], of *Drosophila melanogaster* with the piggyBac vector, pB[PUbDsRed1], having the DsRed1 gene (FIG. 11) (Clontech; Matz et al., 1999) regulated by the *D. melanogaster* polyubiquitin promoter. The hsp70-regulated piggyBac transposase helper was coinjected with the vector. Expression of DsRed1 from the vector construct was tested in preliminary studies by transient expression in *Drosophila* and *Anastrepha suspensa* embryos after injection with a plasmid containing polyubiquitin-regulated DsRed1. For the transformation experiment the pB[PUbDsRed1] vector was mixed with the phsp-pBac helper at concentrations of 600 µg/ml vector and 400 µg/ml helper and injected into 713 eggs of which 305 larvae hatched. Of these, 191 larvae survived to adulthood, including 101 G0 males and 90 G0 females. The G0 adult progeny were backcrossed to w[m] flies in 81 small groups that included either two G0 males (50 groups) or three G0 females (31 groups). All of the groups yielded viable G1 progeny that were screened as larvae, pupae, and adults for DsRed1 expression using a Texas Red filter set (FIGS. 12–15). Of the 81 mating groups, 26 groups yielded G1 progeny expressing red fluorescence. Presuming one G0 transformation event per mating group, and 100% fertility, a minimum frequency of transformation in this experiment is 13.6%. Numerous previous transformation experiments have yielded G0 fertility rates of approximately 50%, which would yield a frequency of about 27% which is similar to previous transformations with the piggyBac vector in *D. melanogaster*.

EXAMPLE 11

*D. melanogaster* was transformed with pB[hsp-GAL4, EGFP] and pB[UAS-DsRed1, EGFP] expression vectors as described above in Example 9. The transformed insects were inbred as single pair matings for successive generations until all progeny expressed the EGFP marker and were considered homozygous. Adult flies from the hsp-Gal4 and UAS-DsRed1 lines were intermated and their progeny subjected to heat shock at about 37° C. for about one hour at indicated times. DsRed expression was monitored at daily intervals.

The use of DsRed as a reporter in an EGFP background was first detected in pharate adult pupae one day after two daily heat shocks (two days after the first heat shock). The ability of filter systems for DsRed to effectively block EGFP fluorescence indicates that DsRed can be used as an unambiguous reporter in tissue where EGFP is co-expressed.

The foregoing detailed description is for the purpose of illustration. Such detail is solely for that purpose and those skilled in the art can make variations without departing from the spirit and scope of the invention.

We claim:

1. A composition for transformation comprising:
   (a) a first DNA comprising a non-transposon heterologous DNA sequence inserted between a pair of inverted repeats of a piggyBac transposon wherein said piggyBac transposon is modified by deleting about 748 bp of internal piggyBac sequence by BglII-HpaI digestion, and at least one sequence encoding a fluorescent protein wherein said at least one sequence encoding a fluorescent protein is operatively linked to a polyubiquitin promoter obtained from *Drosophila melanogaster*, and
   (b) a second DNA encoding a piggyBac transposase that is under control of a heat-shock inducible promoter.

2. A vector comprising:
   (a) a piggyBac transposon having a pair of inverted repeats wherein said transposon is modified by deleting about 748 bp of internal piggyBac sequence by BglII-HpaI digestion,
   (b) a marker cassette inserted into said deleted region wherein said cassette includes a fluorescent protein gene operatively linked to a *Drosophila melanogaster* polyubiquitin promoter, and
   (c) a *Drosophila melanogaster* polyubiquitin promoter operatively linked to said fluorescent protein gene.

* * * * *

SEQUENCE LISTING

<160> NUMBER OF SEQ ID NOS: 14

<210> SEQ ID NO 1
<211> LENGTH: 4
<212> TYPE: DNA
<213> ORGANISM: Trichoplusia ni

<400> SEQUENCE: 1 ttaa                                                                    4

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 2
tcttgacctt gccacagagg                                                  20

<210> SEQ ID NO 3
<211> LENGTH: 20
<212> TYPE: DNA
<213> ORGANISM: Artificial Sequence

```
<220> FEATURE:
<223> OTHER INFORMATION: Description of Artificial Sequence:primer

<400> SEQUENCE: 3
tgacacttac cgcattgaca                                                    20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 4
gtcagtccag aaacaacttt ggc                                                23

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 5
cctcgatata cagaccgata aaaacacatg                                         30

<210> SEQ ID NO 6
<211> LENGTH: 9423
<212> TYPE: DNA
<213> ORGANISM: Artificial Sequence
<220> FEATURE:
<223> OTHER INFORMATION: Description of Artificial
      Sequence:pB[PUb-nls-EGFP]#257

<400> SEQUENCE: 6
gacgaaaggg cctcgtgata cgcctatttt tataggttaa tgtcatgata ataatggttt      60
cttagacgtc aggtggcact tttcggggaa atgtgcgcgg aaccccta tt tgtttatttt    120 tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gttttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
```

-continued

```
tccttttttga taatctcatg accaaaatcc cttaacgtga gttttcgttc cactgagcgt    1200
cagaccccgt agaaaagatc aaggatctt cttgagatcc ttttttttctg cgcgtaatct    1260
gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact caagaactc tgtagcaccg cctacatacc     1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag     1800
gggggcggag cctatggaaa aacgccagca acgcggcctt tttacggttc ctggcctttt    1860
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgaattcgag ctcggtaccc ggggatcctc tagagtcgac ctgcaggcat    2280
gcaagcttgc atgcctgcag gtcgacgctc gcgcgacttg gtttgccatt ctttagcgcg    2340
cgtcgcgtca cacagcttgg ccacaatgtg gtttttgtca aacgaagatt ctatgacgtg    2400
tttaaagttt aggtcgagta aagcgcaaat cttttttaac cctagaaaga tagtctgcgt    2460
aaaattgacg catgcattct tgaaatattg ctctctcttt ctaaatagcg cgaatccgtc    2520
gctgtgcatt taggacatct cagtcgccgc ttggagctcc cgtgaggcgt gcttgtcaat    2580
gcggtaagtg tcactgattt tgaactataa cgaccgcgtg agtcaaaatg acgcatgatt    2640
atcttttacg tgacttttaa gatttaactc atacgataat tatattgtta tttcatgttc    2700
tacttacgtg ataacttatt atatatatat tttcttgtta tagatatcgt gactaatata    2760
taataaaatg ggtagttctt tagacgatga gcatatcctc tctgctcttc tgcaaagcga    2820
tgacgagctt gttggtgagg attctgacag tgaaatatca gatcacgtaa gtgaagatga    2880
cgtccagagc gatacagaag aagcgtttat agatgaggta catgaagtgc agccaacgtc    2940
aagcggtagt gaaatattag acgaacaaaa tgttattgaa caaccaggtt cttcattggc    3000
ttctaacaga atcttgacct tgccacagag gactattaga ggtaagaata acattgttg     3060
gtcaacttca aagtccacga ggcgtagccg agtctctgca ctgaacattg tcagatctcg    3120
agctcaagct tcgaattctg cagtcgacgg tacccgatct tgtcgccgga acgcagcgac    3180
agagattcca atgtgtccgt atcttttcagg cttttgccct tcagttccag acgaagcgac    3240
tggcgattcg cgtgtggggt ctgcttcagg gtcttgtgaa ttagggcgcg cagatcgccg    3300
atgggcgtgg cgccggaggg caccttcacc ttgccgtacg gcttgctgtt cttcgcgttc    3360
aaaatctcca gctccatttt gctttcggtg cgcttgcaat cagtactgtc caaaatcgaa    3420
aatcgccgaa ccgtagtgtg accgtgcggg gctctgcgaa aataaacttt tttaggtata    3480
tggccacaca cggggaaagc acagtggatt atatgtttta atattataat atgcaggttt    3540
```

```
tcattactta tccagatgta agcccactta aagcgattta acaattattt gccgaaagag   3600
taaaaacaaa tttcacttaa aaatggatta agaaaagctt gtgtaagatt atgcgcagcg   3660
ttgccagata gctccattta aaacacttca aaaacaataa gttttgaaaa tatatacata   3720
aatagcagtc gttgccgcaa cgctcaacac atcacacttt taaaacaccc tttacctaca   3780
cagaattact ttttaaattt ccagtcaagc tgcgagtttc aaaattatag ccggtagaga   3840
agacagtgct atttcaaaag caaactaaat aaacaccaat cctaacaagc cttggacttt   3900
tgtaagttta gatcaaaggt ggcattgcat tcaatgtcat ggtaagaagt aggtcgtcta   3960
ggtagaaatc ctcattcagc cggtcaagtc agtacgagaa aggtctcaat ttgaaattgt   4020
cttaaaaata ttttattgtt ttgtactgtg gtgagtttaa acgaaaaaca caaaaaaaaa   4080
gtgatacaca gaaatcataa aaatttttaa tacaaggtat tcgtacgtat caaaaacatt   4140
tcggcacaat ttttttttctc tgtactaaag tgttacgaac actacggtat tttttagtga   4200
ttttcaacgg acaccgaagg tatataaaca gcgttcgcga acggtcgcct tcaaaaccaa   4260
ttgacatttg cagcagcaag tacaagcaga agtaaagcg caatcagcga aaaatttata   4320
cttaattgtt ggtgattaaa gtacaattaa agaacattc tcgaaagtca caagaaacgt   4380
aagtttttaa ctcgctgtta ccaattagta ataagagcaa caagacgttg agtaatttca   4440
agaaaaactg catttcaagg tctttgttcg gccatttttt ttttattcaa cgctctacgt   4500
aattacaaaa taagaaattg gcagccacgc atcttgtttt cccaatcaat tggcatcaaa   4560
acgcaaacaa atctataaat aaaacttgcg tgttgatttt cgccaagatt tattggcaaa   4620
ttgtgaaatt cgcagtgacg catttgaaaa ttcgagaaat cacgaacgca ctcgagcatt   4680
tgtgtgcatg ttattagtta gttagttctt tgcttaattg aagtatttta ccaacgaaat   4740
ccacttattt ttagctgaaa tagagtaggt tgcttgaaac gaaagccacg tctggaaaat   4800
ttcttattgc ttagtagttg tgacgtcacc atatacacac aaaataatgt gtatgcatgc   4860
gtttcagctg tgtatatata catgcacaca ctcgcattat gaaaacgatg acgagcaacg   4920
gaacaggttt ctcaactacc tttgttcctg tttcttcgct ttcctttgtt ccaatattcg   4980
tagagggtta ataggggttt ctcaacaaag ttggcgtcga taaataagtt tcccattttt   5040
attccccagc caggaagtta gtttcaatag ttttgtaatt tcaacgaaac tcatttgatt   5100
tcgtactaat tttccacatc tctatttga cccgcagaat aatccaaaat gcagatcggg   5160
gatcccaccc cacccaagaa gaagcgcaag gtggaggacg atcccgtcgt tttacaacgt   5220
cgtgactggg aaaaccctgg cgttacccaa cttaatcgcc ttgcagcaca tccccctttc   5280
gccagctggc gtaatagcga agaggcccgc accgatcgcc cttcccaaca gttgcggtcg   5340
actctagagg atccccggga tccaccggtc gccaccatgg tgagcaaggg cgaggagctg   5400
ttcaccgggg tggtgcccat cctggtcgag ctggacggcg acgtaaacgg ccacaagttc   5460
agcgtgtccg gcgagggcga gggcgatgcc acctacggca agctgaccct gaagttcatc   5520
tgcaccaccg gcaagctgcc cgtgccctgg cccaccctcg tgaccaccct gacctacggc   5580
gtgcagtgct tcagccgcta ccccgaccac atgaagcagc acgacttctt caagtccgcc   5640
atgcccgaag gctacgtcca ggagcgcacc atcttcttca aggacgacgg caactacaag   5700
acccgcgccg aggtgaagtt cgagggcgac accctggtga accgcatcga gctgaagggc   5760
atcgacttca aggaggacgg caacatcctg ggcacaagc tggagtacaa ctacaacagc   5820
cacaacgtct atatcatggc cgacaagcag aagaacggca tcaaggtgaa cttcaagatc   5880
cgccacaaca tcgaggacgg cagcgtgcag ctcgccgacc actaccagca gaacaccccc   5940
```

-continued

| | | |
|---|---|---|
| atcggcgacg gccccgtgct gctgcccgac aaccactacc tgagcaccca gtccgccctg | 6000 |
| agcaaagacc ccaacgagaa gcgcgatcac atggtcctgc tggagttcgt gaccgccgcc | 6060 |
| gggatcactc tcggcatgga cgagctgtac aagtaaagcg gccgcgactc tagatcataa | 6120 |
| tcagccatac cacatttgta gaggttttac ttgctttaaa aaacctccca cacctccccc | 6180 |
| tgaacctgaa acataaaatg aatgcaattg ttgttgttaa cttgtttatt gcagcttata | 6240 |
| atggttacaa ataaagcaat agcatcacaa atttcacaaa taaagcattt ttttcactgc | 6300 |
| attctagttg tggtttgtcc aaactcatca atgtatctta aggcgtaaat tgtaagcgtt | 6360 |
| aatattttgt taaaattcgc gttaaatttt tgttaaatca gctcattttt taaccaatag | 6420 |
| gccgaaatcg gcaaaatccc ttataaatca aagaataga ccgagatagg gttgagtgtt | 6480 |
| gttccagttt ggaacaagag tccactatta agaacgtgg actccaacgt caagggcga | 6540 |
| aaaccgtct atcagggcga tggcccacta cgtgaaccat caccctaatc aagttttttg | 6600 |
| gggtcgaggt gccgtaaagc actaaatcgg aaccctaaag ggagcccccg atttagagct | 6660 |
| tgacggggaa agccggcgaa cgtggcgaga aggaaggga agaaagcgaa aggagcgggc | 6720 |
| gctagggcgc tggcaagtgt agcggtcacg ctgcgcgtaa ccaccacacc cgccgcgctt | 6780 |
| aatgcgccgc tacagggcgc gtcaggtggc acttttcggg gaaatgtgcg cggaacccct | 6840 |
| atttgtttat ttttctaaat acattcaaat atgtatccgc tcatgagaca ataaccctga | 6900 |
| taaatgcttc aataatattg aaaaaggaag agtcctgagg cggaaagaac cagctgtgga | 6960 |
| atgtgtgtca gttagggtgt ggaaagtccc caggctcccc agcaggcaga agtatgcaaa | 7020 |
| gcatgcatct caattagtca gcaaccaggt gtggaaagtc cccaggctcc ccagcaggca | 7080 |
| gaagtatgca aagcatgcat ctcaattagt cagcaaccat agtcccgccc ctaactccgc | 7140 |
| ccatcccgcc cctaactccg cccagttccg cccattctcc gccccatggc tgactaattt | 7200 |
| tttttattta tgcagaggcc gaggccgcct cggcctctga gctattccag aagtagtgag | 7260 |
| gaggcttttt tggaggaacc attgtgggaa ccgtgcgatc aaacaaacgc gagataccgg | 7320 |
| aagtactgaa aaacagtcgc tccaggccag tgggaacatc gatgtttgt tttgacggac | 7380 |
| cccttactct cgtctcatat aaaccgaagc cagctaagat ggtatactta ttatcatctt | 7440 |
| gtgatgagga tgcttctatc aacgaaagta ccggtaaacc gcaaatggtt atgtattata | 7500 |
| atcaaactaa aggcggagtg gacacgctag accaaatgtg ttctgtgatg acctgcagta | 7560 |
| ggaagacgaa taggtggcct atggcattat tgtacggaat gataaacatt gcctgcataa | 7620 |
| attcttttat tatatacagc cataatgtca gtagcaaggg agaaaggtc caaagtcgca | 7680 |
| aaaaatttat gagaaacctt tacatgagcc tgacgtcatc gtttatgcgt aagcgtttag | 7740 |
| aagctcctac tttgaagaga tatttgcgcg ataatatctc taatattttg ccaaatgaag | 7800 |
| tgcctggtac atcagatgac agtactgaag agccagtaat gaaaaacgt acttactgta | 7860 |
| cttactgccc ctctaaaata aggcgaaagg caaatgcatc gtgcaaaaaa tgcaaaaaag | 7920 |
| ttatttgtcg agagcataat attgatatgt gccaaagttg tttctgactg actaataagt | 7980 |
| ataatttgtt tctattatgt ataagttaag ctaattactt attttataat acaacatgac | 8040 |
| tgtttttaaa gtacaaaata agtttatttt tgtaaaagag agaatgttta aagttttgt | 8100 |
| tactttatag aagaaatttt gagttttgt tttttttaa taaataaata aacataaata | 8160 |
| aattgtttgt tgaatttatt attagtatgt aagtgtaaat ataataaaac ttaatatcta | 8220 |
| ttcaaattaa taaataaacc tcgatataca gaccgataaa acacatgcgt caattttacg | 8280 |
| catgattatc tttaacgtac gtcacaatat gattatcttt ctaggttaa ataatagttt | 8340 |

-continued

```
ctaatttttt tattattcag cctgctgtcg tgaataccgt atatctcaac gctgtctgtg    8400
agattgtcgt attctagcct ttttagtttt tcgctcatcg acttgatatt gtccgacaca    8460
ttttcgtcga tttgcgtttt gatcaaagac ttgagcagag acacgttaat caactgttca    8520
aattgatcca tattaacgat atcaacccga tgcgtatatg gtgcgtaaaa tatatttttt    8580
aaccctctta tactttgcac tctgcgttaa tacgcgttcg tgtacagacg taatcatgtt    8640 ttctttttg gataaaactc ctactgagtt tgacctcata ttagaccctc acaagttgca     8700
aaacgtggca tttttacca atgaagaatt taaagttatt ttaaaaatt tcatcacaga      8760 tttaaagaag aaccaaaaat taaattattt caacagttta atcgaccagt taatcaacgt    8820
gtacacagac gcgtcggcaa aaaacacgca gcccgacgtg ttggctaaaa ttattaaatc    8880
aacttgtgtt atagtcacgg atttgccgtc caacgtgttc ctcaaaaagt tgaagaccaa    8940
caagtttacg gacactatta attatttgat tttgccccac ttcattttgt gggatcacaa    9000
ttttgttata tttaaacaa agcttggcac tggccgtcgt tttacaacgt cgtgactggg     9060
aaaaccctgg cgttacccaa cttaatcgcc ttgcagcaca tcccccttc gccagctggc     9120 gtaatagcga agaggcccgc accgatcgcc cttcccaaca gttgcgcagc ctgaatggcg    9180
aatggcgcct gatgcggtat tttctcctta cgcatctgtg cggtatttca caccgcatat    9240
ggtgcactct cagtacaatc tgctctgatg ccgcatagtt aagccagccc cgacacccgc    9300
caacacccgc tgacgcgccc tgacgggctt gtctgctccc ggcatccgct tacagacaag    9360
ctgtgaccgt ctccgggagc tgcatgtgtc agaggttttc accgtcatca ccgaaacgcg    9420
cga                                                                 9423
```

```
<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:p3E1.2

<400> SEQUENCE: 7
aagcgcaaat cttttttaa                                                 19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:p3E1.2

<400> SEQUENCE: 8
ttaaataata gtttctaat                                                 19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:F1-2

<400> SEQUENCE: 9
aaaaagactg actatttaa                                                 19

<210> SEQ ID NO 10
<211> LENGTH: 19
<212> TYPE: DNA
<213> ORGANISM: Artificial Sequence
```

```
<220> FEATURE:
<223> OTHER INFORMATION: Description of Artificial Sequence:F1-2

<400> SEQUENCE: 10
ttaataagca cactgagtc                                                     19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:M17-4

<400> SEQUENCE: 11
aaaatgtcgt ctaggttaa                                                     19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:M17-4

<400> SEQUENCE: 12
ttaaagccgt atatcagat                                                     19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:M31-6

<400> SEQUENCE: 13
aaatgaacga cttttttaa                                                     19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:M31-6

<400> SEQUENCE: 14
ttaatggttt tttagttgt                                                     19
```